United States Patent [19]

Yanai et al.

[11] Patent Number: 5,276,033

[45] Date of Patent: Jan. 4, 1994

[54] 13-(SUBSTITUTED THIO)ACETOXYMILBEMYCIN DERIVATIVES, THEIR PREPARATION AND THEIR AGROCHEMICAL USES

[75] Inventors: Toshiaki Yanai; Soji Sugai; Hideo Takeshiba; Junzo Tobitsuka; Kazuo Sato; Shinji Yokoi; Shinya Niimi, all of Shiga; Akio Saito, Tokyo, all of Japan

[73] Assignee: Sankyo Company, Limited, Tokyo, Japan

[21] Appl. No.: 992,865

[22] Filed: Dec. 17, 1992

[51] Int. Cl.$^5$ .................. A61K 31/53; A61K 31/505; C07D 239/38

[52] U.S. Cl. .................... 514/241; 514/242; 514/252; 514/253; 514/269; 514/274; 544/182; 544/216; 544/217; 544/218; 544/219; 544/230

[58] Field of Search ............... 514/241, 242, 252, 253, 514/274; 544/182, 216, 217, 218, 219, 230, 238, 295, 296, 298, 299, 300, 309, 310, 315, 316, 318, 319, 336; 549/264, 265

[56] References Cited

U.S. PATENT DOCUMENTS

| | | | |
|---|---|---|---|
| 3,950,360 | 4/1976 | Aoki et al. | 424/274 |
| 4,171,314 | 10/1979 | Chabala et al. | 536/17 |
| 4,173,571 | 11/1979 | Chabala et al. | 536/17 |
| 4,201,861 | 5/1980 | Mrozik et al. | 536/17 |
| 4,203,976 | 5/1980 | Fisher et al. | 536/17 |
| 4,206,205 | 6/1980 | Mrozik et al. | 424/180 |
| 4,289,760 | 9/1981 | Mrozik et al. | 536/17 |
| 4,346,171 | 8/1982 | Takiguchi et al. | 435/119 |
| 4,423,209 | 12/1983 | Mrozik | 549/264 |
| 4,457,920 | 7/1984 | Mrozik | 546/15 |
| 4,547,491 | 10/1985 | Mrozik et al. | 514/30 |
| 4,547,520 | 10/1985 | Ide et al. | 549/264 |
| 4,579,864 | 4/1986 | Linn et al. | 514/450 |
| 4,696,922 | 9/1987 | Sturm et al. | 514/185 |
| 4,945,105 | 7/1990 | Sato et al. | 514/450 |

FOREIGN PATENT DOCUMENTS 0444964 9/1991 European Pat. Off. .
0448243 9/1991 European Pat. Off. .

Primary Examiner—Mukund J. Shah
Assistant Examiner—Y. N. Gupta
Attorney, Agent, or Firm—Frishauf, Holtz, Goodman & Woodward

[57] ABSTRACT

Compounds having the formula (I)

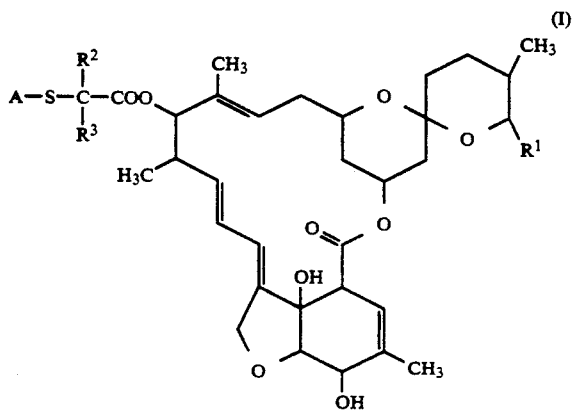

wherein: $R^1$ is methyl, ethyl or isopropyl; $R^2$ is alkyl, aralkyl, cycloalkyl, cycloalkylmethyl, aryl, heterocyclic, or heterocyclic-substituted thio; $R^3$ is hydrogen, methyl or ethyl; or $R^2$ together with $R^3$ is —$(CH_2)_n$—, wherein n is 3, 4 or 5; and A is aromatic heterocyclic; and salts thereof, are valuable agricultural and horticultural anthelmintic, acaricidal and insecticidal agents.

36 Claims, No Drawings

13-(SUBSTITUTED THIO)ACETOXYMILBEMYCIN DERIVATIVES, THEIR PREPARATION AND THEIR AGROCHEMICAL USES

BACKGROUND TO THE INVENTION

The present invention relates to a series of new derivatives of the compounds known as the "milbemycins", which derivatives are characterised by the presence of a heterocyclic-substituted mercaptoacetoxy group at the 13-position. The invention also provides new methods and compositions using these compounds for agricultural and horticultural purposes, as well as processes for preparing them.

There are several classes of known compounds with a structure based on a 16-membered macrolide ring, which compounds are obtained by fermentation of various microorganisms or are obtained semi-synthetically by chemical derivatization of such natural fermentation products, and which exhibit acaricidal, insecticidal, anthelmintic and antiparasitic activities. The milbemycins and avermectins are examples of two such classes of known compounds, but various others also exist and are identified in the art by different names or code numbers. The names for these various macrolide compounds have generally been taken from the names or code numbers of the microorganisms which produce the naturally occurring members of each class, and these names have then been extended to cover the chemical derivatives of the same class, with the result that there has been no standardized systematic nomenclature for such compounds generally.

In order to avoid confusion, a standardized system of nomenclature will be used herein, which follows the normal rules for naming derivatives of organic compounds as recommended by the International Union of Pure and Applied Chemistry (IUPAC), Organic Chemistry Division, Commission on Nomenclature of Organic Chemistry, and which is based primarily on the hypothetical parent compound hereby defined as "milbemycin" and represented by the formula (II):

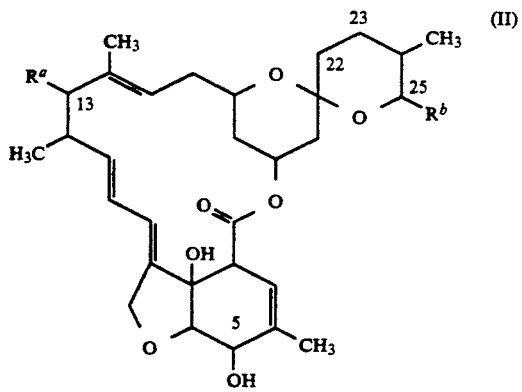

wherein $R^1$ and $R^b$ both represent hydrogen atoms.

For the avoidance of doubt, formula (II) also shows the numbering of positions of the macrolide ring system applied to those positions most relevant to the compounds of the present invention and of the prior art.

The naturally produced milbemycins are a series of macrolide compounds known to have anthelmintic, acaricidal and insecticidal activities. Milbemycin D was disclosed in U.S. Pat. No. 4,346,171, where it was referred to as "Compound B-41D", and milbemycins $A_3$ and $A_4$ were disclosed in U.S. Pat. No. 3,950,360. These compounds may be represented by the above formula (II) in which $R^a$ at position 13 is a hydrogen atom and $R^b$ at position 25 is a methyl group, an ethyl group or an isopropyl group, these compounds being designated as milbemycin $A_3$, milbemycin $A_4$ and milbemycin D, respectively. The milbemycin analog having a hydrogen atom at position 13 and substituted at position 25 with a sec-butyl group was disclosed in U.S. Pat. No. 4,173,571, where it was known as "13-deoxy-22,23-dihydroavermectin $B_{1a}$ aglycone".

Subsequently, various derivatives of the original milbemycins and avermectins have been prepared and their activities investigated. For example, 5-esterified milbemycins have been disclosed in U.S. Pat. No. 4,201,861, No. 4,206,205, No. 4,173,571, No. 4,171,314, No. 4,203,976, No. 4,289,760, No. 4,457,920, No. 4,579,864 and No. 4,547,491, in European Patent Publications No. 8184, No. 102,721, No. 115,930, No. 180,539 and No. 184,989 and in Japanese Patent Applications Kokai (i.e. as laid open to public inspection) No. 57-120589 and 59-16894.

13-Hydroxy-5-ketomilbemycin derivatives have been disclosed in U.S. Pat. No. 4,423,209. Milbemycin 5-oxime derivatives were disclosed in U.S. Pat. No. 4,547,520 and in European Patent Publication No. 203 832.

Milbemycins having an ester bond at the 13 position are of particular relevance to the present invention and a number of compounds in which the 13-hydroxy group in the compounds of the above formula (II) has been esterified is disclosed in Japanese Patent Kokai Application No. Sho 61-180787, which describes esters of a variety of carboxylic acids such as the alkanoic acids. However, the carboxylic acid moiety at the 13-position of these prior art compounds does not include any heterocyclic rings. Other milbemycin derivatives having an ester bond at the 13-position are described in Japanese Patent Kokai Application No. Hei 1-104078, which is considered by us to represent the closest prior art to the compounds of the present invention. In this document there are disclosed compounds in which the carboxylic acid moiety has a side chain, such as an alkyl group, at the α-position of the carboxylic acid group.

The various classes of milbemycin-related macrolide compounds referred to above are all disclosed as having one or more types of activity as antibiotic, anthelmintic, ectoparasiticidal, acaricidal or other pesticidal agents. However, there is still a continuing need to provide such agents with improved activity against one or more classes of agricultural and horticulural pests.

It has now been discovered that the activity of such milbemycin-related derivatives can be improved by appropriately selecting the combination of substituents on the macrolide ring system, especially the substituents at position 13. In particular, it has now been found that the activity of the compounds can be improved upon by appropriate selection of certain highly specific ester groups at the 13 position, as specified below. In general, the compounds of the present invention tend to have a better pesticidal activity than do the compounds of the prior art, and many of the compounds of the present invention have a very substantially better activity.

BRIEF SUMMARY OF INVENTION

Accordingly, it is an object of the present invention to provide such macrolide compounds having improved activity. It is another object of the invention to provide methods for preparing such compounds. It is a still further object of the invention to provide pesticidal compositions and methods using the said compounds.

In accordance with these objects, the invention provides compounds having the formula (I):

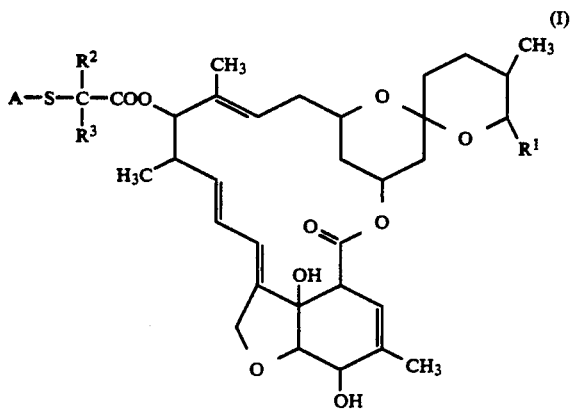

wherein:
$R^1$ represents a methyl, ethyl or isopropyl group;
$R^2$ represents:
  an alkyl group having from 1 to 6 carbon atoms;
  an aralkyl group, in which an alkyl group having from 1 to 3 carbon atoms is substituted by at least one carbocyclic aryl group having from 6 to 10 carbon atoms, said aryl group being unsubstituted or being substituted by at least one substituent selected from the group consisting of methyl and ethyl groups;
  a cycloalkyl group having from 3 to 6 carbon atoms;
  a cycloalkylmethyl group in which the cycloalkyl part has from 3 to 6 carbon atoms;
  a carbocyclic aryl group which has from 6 to 10 ring carbon atoms and which is unsubstituted or is substituted by at least one substituent selected from the group consisting of methyl groups, ethyl groups, a haloalkyl group having 1 or 2 carbon atoms, methoxy groups, ethoxy groups, halogen atoms and amino groups;
  a heterocyclic group in which a 5- or 6-membered alicyclic ring containing 1 or 2 oxygen atoms is condensed with benzene ring; or
  a group of formula $R^4$—S—, in which $R^4$ represents a 6-membered aromatic heterocyclic group containing 2 nitrogen atoms;
$R^3$ represents a hydrogen atom, a methyl group or an ethyl group; or
$R^2$ together with $R^3$ represents a group of formula —$(CH_2)_n$—, wherein n represents the integer 3,4 or 5; and
A represents a 6-membered aromatic heterocyclic group containing 2 or 3 nitrogen atoms which is unsubstituted or is substituted by at least one substituent selected from the group consisting of alkyl groups having from 1 to 4 carbon atoms, methoxy groups, ethoxy groups and halogen atoms;
and salts thereof.

The invention still further provides an anthelmintic, acaricidal and insecticidal composition comprising an anthelmintic, acaricidal and insecticidal compound in admixture with an agriculturally or horticulturally acceptable carrier or diluent, wherein said compound is selected from the group consisting of compounds of formula (I) and salts thereof.

The invention still further provides a method of protecting plants from damage by parasites selected from the group consisting of acarids, helminths and insects, which comprises applying an active compound to said plants or to parts of or reproductive matter (e.g. seeds) of said plants or to a locus including said plants or parts of said plants or reproductive matter of said plants, wherein the active compound is selected from the group consisting of compounds of formula (I) and salts thereof.

DETAILED DESCRIPTION OF INVENTION

In the compounds of the present invention, where $R^2$ represents an alkyl group having from 1 to 6 carbon atoms, this may be a straight or branched chain group having from 1 to 6 carbon atoms, and examples include the methyl, ethyl, propyl, isopropyl, butyl, isobutyl, sec-butyl, t-butyl, pentyl, isopentyl, neopentyl, t-pentyl, 2-methylbutyl, 1-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 3 to 5 carbon atoms, more preferably the isopropyl and 1-methylbutyl groups, and most preferably the isopropyl group.

Where $R^2$ represents a cycloalkyl group, this has from 3 to 6 carbon atoms, and examples of such groups include the cyclopropyl, cyclobutyl, cyclopentyl and cyclohexyl groups, of which we prefer those cycloalkyl groups having 5 or 6 carbon atoms, and most prefer the cyclohexyl group.

Where $R^2$ represents a cycloalkylmethyl group, this has from 3 to 6 carbon atoms in the cycloalkyl moiety, that is it has a total of from 4 to 7 carbon atoms. Examples of such groups include the cyclopropylmethyl, cyclobutylmethyl, cyclopentylmethyl and cyclohexylmethyl groups, of which we prefer those cycloalkylmethyl groups having 5 or 6 carbon atoms in the cycloalkyl moiety, and more prefer the cyclohexylmethyl group.

Where $R^2$ represents an aryl group, this is a carbocyclic aromatic group having from 6 to 10 ring carbon atoms which group is unsubstituted or is substituted by at least one substituent selected from the group consisting of methyl groups, ethyl groups, haloalkyl groups having 1 or 2 carbon atoms, methoxy groups, ethoxy groups, halogen atoms and amino groups. There is no particular limitation on the number of these substituents, except such as may be imposed by the number of substitutable positions and possibly by steric constraints. However, in general, from 1 to 5 substituents are preferred, from 1 to 3 being more preferred and 1 or 2 being most preferred. Examples of these substituents include:
  alkyl groups having 1 or 2 carbon atoms, that is the methyl and ethyl groups, preferably the methyl group; haloalkyl groups having 1 or 2 carbon atoms, and preferably from 1 to 5, more preferably from 1 to 3 halogen atoms, such as the fluoromethyl, chloromethyl, bromomethyl, difluoromethyl, trifluoromethyl, trichloromethyl, tribromomethyl, 2-fluoroethyl, 2,2,2-trifluoroethyl, 2,2,2-trichloroethyl and 2,2,2-tribromoethyl groups, of which we prefer those fluoroalkyl groups having 1 or 2 carbon atoms, and more prefer the trifluoromethyl group;

alkoxy groups having 1 or 2 carbon atoms, that is the methoxy and ethoxy groups, preferably the methoxy group; and halogen atoms, which may be the fluorine, chlorine, bromine or iodine atoms, preferably the bromine or fluorine atoms, and more preferably the fluorine atom.

The aryl groups represented by $R^2$ may have from 6 to 10, preferably 6 or 10, ring carbon atoms, and examples include the phenyl, 1-naphthyl and 2-naphthyl groups, preferably the phenyl group. The number of substituents on these aryl groups is preferably 0, 1 or 2, and most preferably 0. In the case of the phenyl group, if the number of substituents is 1, the substituent is preferably on the 2- or the 4-position, more preferably on the 2-position; on the other hand, if the number of substituents is 2, they are preferably on the 2- and 4-, or on the 2- and 6-, positions, more preferably on the 2- and 6-positions.

Where $R^2$ represents an aralkyl group, this is an alkyl group having from 1 to 3, preferably 1 or 2, carbon atoms substituted by one or two, preferably one, aryl group, and the aryl group is as defined and exemplified above. The aralkyl group as a whole preferably has from 7 to 12 carbon atoms. The aryl part of the aralkyl group may be unsubstituted or it may be substituted by at least one, and preferably 1 or 2, substituent selected from the group consisting of methyl and ethyl groups. Examples of the unsubstituted groups include the benzyl, α-methylbenzyl, phenethyl, 1-naphthylmethyl, 2-naphthylmethyl and 2-(1-naphthyl)ethyl groups, of which we prefer the benzyl group.

Where $R^2$ represents a heterocyclic group in which a 5- or 6-membered alicyclic ring containing 1 or 2 oxygen atoms (the remaining ring atoms being carbon atoms) is condensed with a benzene ring, this may be, for example, a 1-dihydrobenzopyran-5-yl, 1-dihydrobenzopyran-2-yl, 1-dihydrobenzofuran-6-yl, 1-dihydrobenzofuran-2-yl, 1,3-benzodioxolan-5-yl, 1,4-benzodioxan-6-yl or 1,3-benzodioxan-6-yl group, of which we prefer those heterocyclic groups in which a 5- or 6-membered alicyclic ring containing 2 oxygen atoms is condensed with a benzene ring. The most preferred of these groups are the 1,3-benzodioxolan-5-yl, 1,4-benzodioxan-6-yl and 1,3-benzodioxan-6-yl groups.

Where $R^2$ represents a group of formula $R^4$-S-, $R^4$ represents a 6-membered aromatic heterocyclic group containing 2 nitrogen atoms (the remaining ring atoms being carbon atoms), and examples of such groups include the 3-pyridazinyl, 4-pyridazinyl, 2-pyrimidinyl, 4-pyrimidinyl, 5-pyrimidinyl, 2-pyrazinyl and 3-pyrazinyl groups, of which we prefer the 2-pyrimidinyl, 4-pyrimidinyl and 5-pyrimidinyl groups, and more prefer the 2-pyrimidinyl group.

Where A in the compounds of formula (I) represents a 6-membered aromatic heterocyclic group containing 2 or 3 nitrogen atoms (the remaining ring atoms being carbon atoms), this group may be unsubstituted or it may be substituted by at least one substituent selected from the group consisting of alkyl groups having from 1 to 4 carbon atoms, alkoxy groups having 1 or 2 carbon atoms and halogen atoms. Examples of such substituents include:

alkyl groups having from 1 to 4 carbon atoms, which may be straight or branched chain alkyl groups, such as the methyl, ethyl, propyl, isopropyl, butyl, isobutyl, sec-butyl and t-butyl groups, of which we prefer those alkyl groups having 1 or 2 carbon atoms, more preferably the methyl group;

alkoxy groups having 1 or 2 carbon atoms, that is the methoxy or ethoxy groups, preferably the methoxy group; and halogen atoms, for example, the fluorine, chlorine, bromine or iodine atoms, preferably the fluorine or chlorine atoms, and more preferably the chlorine atom.

The aromatic heterocyclic group has 6 ring atoms, of which 2 or 3 are nitrogen atoms and the remainder are carbon atoms, and examples of the unsubstituted groups include the 3-pyridazinyl, 4-pyridazinyl, 2-pyrimidinyl, 4-pyrimidinyl, 5-pyrimidinyl, 2-pyrazinyl, 3-pyrazinyl, 2-(1,3,5-)triazinyl, 3-(1,2,4-)triazinyl, 5-(1,2,4-)triazinyl and 6-(1,2,4-)triazinyl groups, of which we prefer those 6-membered aromatic heterocyclic groups containing 2 nitrogen atoms, more preferably the pyrimidinyl groups, and most preferably the 2-pyrimidinyl group.

There is no particular limitation on the number of substituents, except such as may be imposed by the number of substitutable positions and possibly by steric constraints. However, in general, where the heterocyclic group is substituted, from 1 to 3 substituents are preferred, 0, 1 or 2 substituents being more preferred, and 0 or 1 being still more preferred; most preferably, however, the group is unsubstituted.

The compounds of the present invention may contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques. In particular, the compounds of the present invention can exist in the α- or β-configuration with respect to the stereochemistry of the 13-position of the milbemycin skelton. Although all such isomers and mixtures thereof form a part of the present invention, the preferred configuration is the β-configuration.

Preferred classes of compounds of the present invention are those compounds of formula (I) in which:
(A) $R^2$ represents:
an alkyl group having from 2 to 5 carbon atoms;
an arylmethyl group in which the aryl part has from 6 to 10 carbon atoms;
a cycloalkyl group having 5 or 6 carbon atoms;
a cycloalkylmethyl group in which the cycloalkyl part has 5 or 6 carbon atoms;
a phenyl group or a 2-naphthyl group which is unsubstituted or is substituted by 1 or 2 substituents selected from the group consisting of methyl groups, trifluoromethyl groups, methoxy groups, fluorine atoms, chlorine atoms and amino groups;

a benzene ring condensed with a 5 or 6-membered alicyclic group containing 1 or 2 oxygen atoms; or a 6-membered aromatic heterocyclic group containing 2 nitrogen atoms.

(B) $R^3$ represents a hydrogen atom, a methyl group or an ethyl group.

(C) instead of (A) or (B), the group of formula —$(CH_2)_n$—, which is formed by $R^2$ together with $R^3$, is a trimethylene group.

(D) A represents a 6-membered aromatic heterocyclic group containing 2 or 3 nitrogen atoms which is unsubstituted or is substituted by at least one substituent selected from the group consisting of methyl groups, ethyl groups, methoxy groups, ethoxy groups and halogen atoms.

In particular, of the above classes of compounds, we prefer those in which $R^2$ is as defined in (A) above, $R^3$ is as defined in (B) above, or $R^2$ and $R^3$ together are as defined in (C) above, and A is as defined in (D) above.

More preferred classes of compounds of the present invention are those compounds of formula (I) in which:

(E) $R^1$ represents a methyl or ethyl group.

(F) $R^2$ represents: an alkyl group having from 3 to 5 carbon atoms; a 1-methylbenzyl group; a phenyl group which is unsubstituted or is substituted by 1 or 2 substituents selected from the group consisting of methyl groups, trifluoromethyl groups, methoxy groups, fluorine atoms, chlorine atoms and amino groups; a 2-naphthyl group; a 1,3-benzodioxolan-5-yl group; or a 1,4-benzodioxan-6-yl group.

(G) $R^3$ represents a hydrogen atom.

(H) A represents a 3-pyridazinyl group, a 2-pyridazinyl group, a 4-pyrimidinyl group, a 2-pyrazinyl group or a 1,3,5-triazin-2-yl group, each of which is unsubstituted or is substituted by 1 or 2 substituents selected from the group consisting of methyl groups, ethyl groups, methoxy groups, ethoxy groups and halogen atoms.

In particular, of the above classes of compounds, we prefer those in which $R^1$ is as defined in (E) above, $R^2$ is as defined in (F) above, $R^3$ is as defined in (G) above, and A is as defined in (H) above.

Still more preferred classes of compounds of the present invention are those compounds of formula (I) in which:

(I) $R^2$ represents an isopropyl group or a phenyl group which is unsubstituted or is substituted by 1 or 2 substituents selected from the group consisting of methyl groups, trifluoromethyl groups, fluorine atoms and chlorine atoms at the 2-position and/or 6-position of the phenyl group.

(J) A represents a 2-pyrimidinyl group.

In particular, of the above classes of compounds, we prefer those in which $R^1$ is as defined in (E) above, $R^2$ is as defined in (I) above, $R^3$ is as defined in (G) above, and A is as defined in (J) above, and, in relation to all of the classes of compounds (A) to (J) above, those in which the carbon atom at the 13-position is in the β-configuration.

The most preferred compounds of the present invention are (K) those in which $R^2$ represents an isopropyl or phenyl group, and most especially those in which $R^1$ is as defined in (E) above, $R^2$ is as defined in (K) above, $R^3$ is as defined in (G) above, and A is as defined in (J) above, and particularly those in which the carbon atom at the 13-position is in the β-configuration.

Those compounds of the present invention which contain one or more basic nitrogen atoms (for example those in which $R^2$ represents a group of formula $R^4$—S—, where $R^4$ represents a 6-membered aromatic heterocyclic group containing 2 nitrogen atoms) can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

Specific examples of compounds of the invention are those compounds of formula (I) in which $R^1$, $R^2$ and A are as defined in Table 1 below. The number of each compound has a prefix, K, L, M or N, which indicates the definition of $R^3$. Thus, in those compounds where the prefix is K, $R^3$ represents a hydrogen atom; in those compounds where the prefix is L, $R^3$ represents a methyl group; in those compounds where the prefix is M, $R^3$ represents an ethyl group; and, in those compounds where the prefix is N, $R^2$ together with $R^3$ represents a group of formula —$(CH_2)_n$—, and in this case, specific examples of this group are shown in the $R^2$ column. In addition, where "optical isomer" is referred to in the $R^2$ column, the respective compound can exist as optical isomers due to the carbon atom to which $R^2$ and $R^3$ are attached; for any compound whose absolute configuration is established, R or S is also indicated. Where the presence of optical isomers has been confirmed, but the absolute configuration has not been established, the isomers are identified as "A" and "B".

TABLE 1

| Cpd. No. | $R^1$ | $R^2$ | A |
|---|---|---|---|
| K-1 | ethyl | ethyl | 2-pyrimidinyl |
| K-2 | ethyl | propyl | 2-pyrimidinyl |
| K-3 | ethyl | isopropyl | 2-pyrimidinyl |
| K-4 | ethyl | butyl | 2-pyrimidinyl |
| K-5 | ethyl | sec-butyl | 2-pyrimidinyl |
| K-6 | ethyl | cyclopentyl | 2-pyrimidinyl |
| K-7 | ethyl | cyclohexyl | 2-pyrimidinyl |
| K-8 | ethyl | phenyl | 2-pyrimidinyl |
| K-9 | ethyl | 2-tolyl | 2-pyrimidinyl |
| K-10 | ethyl | 4-chlorophenyl | 2-pyrimidinyl |
| K-11 | ethyl | 2-chlorophenyl | 2-pyrimidinyl |
| K-12 | ethyl | 4-aminophenyl | 2-pyrimidinyl |
| K-13 | ethyl | 2-fluorophenyl | 2-pyrimidinyl |
| K-14 | ethyl | 2-trifluoromethylphenyl | 2-pyrimidinyl |
| K-15 | ethyl | 2,6-difluorophenyl | 2-pyrimidinyl |
| K-16 | ethyl | isopropyl | 4-methyl-2-pyrimidinyl |
| K-17 | ethyl | phenyl | 4-methyl-2-pyrimidinyl |
| K-18 | ethyl | 4-chlorophenyl | 4-methyl-2-pyrimidinyl |
| K-19 | ethyl | 2-chlorophenyl | 4-methyl-2-pyrimidinyl |
| K-20 | ethyl | 2-fluorophenyl | 4-methyl-2-pyrimidinyl |
| K-21 | ethyl | isopropyl | 5-methyl-2-pyrimidinyl |
| K-22 | ethyl | phenyl | 5-methyl-2-pyrimidinyl |
| K-23 | ethyl | 2-tolyl | 5-methyl-2-pyrimidinyl |

TABLE 1-continued

| Cpd. No. | R¹ | R² | A |
|---|---|---|---|
| K-24 | ethyl | 4-chlorophenyl | 5-methyl-2-pyrimidinyl |
| K-25 | ethyl | 2-chlorophenyl | 5-methyl-2-pyrimidinyl |
| K-26 | ethyl | 2-fluorophenyl | 5-methyl-2-pyrimidinyl |
| K-27 | ethyl | isopropyl | 4,6-dimethyl-2-pyrimidinyl |
| K-28 | ethyl | phenyl | 4,6-dimethyl-2-pyrimidinyl |
| K-29 | ethyl | 2-tolyl | 4,6-dimethyl-2-pyrimidinyl |
| K-30 | ethyl | 4-chlorophenyl | 4,6-dimethyl-2-pyrimidinyl |
| K-31 | ethyl | 2-chlorophenyl | 4,6-dimethyl-2-pyrimidinyl |
| K-32 | ethyl | 2-fluorophenyl | 4,6-dimethyl-2-pyrimidinyl |
| K-33 | ethyl | isopropyl | 5-chloropyrimidinyl |
| K-34 | ethyl | phenyl | 5-chloropyrimidinyl |
| K-35 | ethyl | 4-chlorophenyl | 5-chloropyrimidinyl |
| K-36 | ethyl | 2-chlorophenyl | 5-chloropyrimidinyl |
| K-37 | ethyl | isopropyl | 4-pyrimidinyl |
| K-38 | ethyl | phenyl | 4-pyrimidinyl |
| K-39 | ethyl | isopropyl | 2-pyrazinyl |
| K-40 | methyl | isopropyl | 2-pyrimidinyl |
| K-41 | methyl | cyclopentyl | 2-pyrimidinyl |
| K-42 | methyl | phenyl | 2-pyrimidinyl |
| K-43 | isopropyl | isopropyl | 2-pyrimidinyl |
| K-44 | ethyl | cyclopentyl | 5-methyl-2-pyrimidynyl |
| K-45 | ethyl | cyclopentyl | 5-chloro-2-pyrimidinyl |
| K-46 | ethyl | cyclopentyl | 4,6-dimethyl-2-pyrimidinyl |
| K-47 | ethyl | cylcopentyl | 4-methyl-2-pyrimidinyl |
| K-48 | ethyl | cyclohexyl | 2-pyrimidinyl |
| K-49 | ethyl | cyclohexyl | 4-methyl-2-pyrimidinyl |
| K-50 | ethyl | 2,6-difluorophenyl | 5-chloro-2-pyrimidinyl |
| K-51 | ethyl | 2,6-difluorophenyl | 5-methyl-2-pyrimidinyl |
| K-52 | ethyl | 2,6-difluorophenyl | 4-methyl-2-pyrimidinyl |
| K-53 | ethyl | 2,6-difluorophenyl | 4,6-dimethyl-2-pyrimidinyl |
| K-54 | ethyl | cyclohexyl | 5-methyl-2-pyrimidinyl |
| K-55 | ethyl | cyclohexyl | 5-chloro-2-pyrimidinyl |
| K-56 | ethyl | cyclohexyl | 2-pyrazinyl |
| K-57 | ethyl | phenyl | 2-pyrazinyl |
| K-58 | ethyl | cylcopentyl | 2-pyrazinyl |
| K-59 | ethyl | cyclopentylmethyl | 2-pyrimidinyl |
| K-60 | ethyl | cyclohexylmethyl | 2-pyrimidinyl |
| K-61 | ethyl | 1-methylbutyl | 2-pyrimidinyl |
| K-62 | ethyl | phenyl | 3-pyridazinyl |
| K-63 | ethyl | isopropyl | 3-pyridazinyl |
| K-64 | ethyl | 1,3-benzodioxolan-5-yl | 2-pyrimidinyl |
| K-65 | ethyl | 2-naphthyl | 2-pyrimidinyl |
| K-66 | ethyl | phenyl | 4,6-dimethoxy-1,3,5-triazin-2-yl |
| K-67 | ethyl | phenyl (optical isomer, S) | 2-pyrimidinyl |
| K-68 | ethyl | phenyl (optical isomer, R) | 2-pyrimidinyl |
| K-69 | ethyl | 1,4-benzodioxan-6-yl | 2-pyrimidinyl |
| K-70 | ethyl | phenyl | 6-methoxy-3-pyridazinyl |
| K-71 | ethyl | isopropyl | 6-methoxy-3-pyridazinyl |
| K-72 | ethyl | phenyl | 6-chloro-3-pyridazinyl |
| K-73 | ethyl | isopropyl | 6-chloro-3-pyridazinyl |
| K-74 | ethyl | phenyl | 6-methyl-3-pyridazinyl |
| K-75 | ethyl | isopropyl | 6-methyl-3-pyridazinyl |
| L-76 | ethyl | methyl | 2-pyrimidinyl |
| K-77 | ethyl | isopropyl (optical isomer, R) | 2-pyrimidinyl |
| K-78 | ethyl | isopropyl (optical isomer, S) | 2-pyrimidinyl |
| N-79 | ethyl | —(CH₂)₄— | 2-pyrimidinyl |
| M-80 | ethyl | ethyl | 2-pyrimidinyl |
| N-81 | ethyl | —(CH₂)₃— | 2-pyrimidinyl |
| K-82 | ethyl | 2-chlorophenyl (optical isomer A) | 3-pyridazinyl |
| K-83 | ethyl | 2-chlorophenyl (optical isomer B) | 3-pyridazinyl |
| K-84 | ethyl | 2 chlorophenyl | 6-methyl-3-pyridazinyl |
| N-85 | ethyl | —(CH₂)₅— | 2-pyrimidinyl |
| K-86 | ethyl | phenyl | 3,6-dimethyl-2-pyrazinyl |
| K-87 | ethyl | phenyl | 5-ethyl-2-pyrimidinyl |
| K-88 | ethyl | phenyl | 5-bromo-2-pyrimidinyl |
| K-89 | ethyl | 4-methoxyphenyl | 2-pyrimidinyl |
| K-90 | ethyl | α-methylbenzyl | 2-pyrimidinyl |
| K-91 | ethyl | 2-methoxyphenyl | 2-pyrimidinyl |
| K-92 | ethyl | phenyl | 6-methyl-1,2,4-triazin-5-yl |
| K-93 | ethyl | phenyl | 5-methyl-1,2,4-triazin-6-yl |
| K-94 | ethyl | 2-pyrimidinylthio | 2-pyrimidinyl |

Of the compounds listed above, the following are preferred, that is to say, Compounds No. K-1, K-2, K-3, K-4, K-5, K-6, K-7, K-8, K-9, K-10, K-11, K-12, K-13, K-14, K-15, K-16, K-17, K-18, K-19, K-20, K-21, K-22, K-23, K-24, K-25, K-26, K-27, K-28, K-32, K-33, K-34, K-38, K-39, K-40, K-42, K-43, K-44, K-45, K-46, K-47, K-48, K-49, K-50, K-51, K-52, K-53, K-54, K-56, K-57, K-59, K-60, K-61, K-62, K-63, K-64, K-66, K-67, K-68, K-69, K-70, K-71, K-72, K-73, K-74, K-75, K-76, K-77, K-78, N-79, M-80, N-81, K-82, K-83, K 85, K-76, K-88, K-90 and K-93, and the following are more preferred ones: Compounds No. K-3, K-4, K-6, K-7, K-8, K-9, K-11, K-13, K-14, K-16, K-21, K-22, K-25, K-28, K-40, K-42, K-43, K-44, K-47, K-51, K-59, K-61, K-62, K-64, K-66, K-67, K-68, K-69, K-74, K-77, K-78, K-79, M-80, N-81, K-84 and K-88.

Still more preferred individual compounds are Compounds No.:

K-3. 13-[3-Methyl-2-(2-pyrimidinylthio)butyryloxy]-milbemycin A₄;

K-8. 13-[2-Phenyl-2-(2-pyrimidinylthio)acetoxy]milbemycin A₄;

K-40. 13-[3-Methyl-2-(2-pyrimidinylthio)butyryloxy]-milbemycin A₃;

K-42. 13-[2-Phenyl-2-(2-pyrimidinylthio)acetoxy]milbemycin A₃;

K-67. 13-[(2S)-2-Phenyl-2-(2-pyrimidinylthio)acetoxy]-milbemycin A₄;

K-68. 13-[(2R)-2-Phenyl-2-(2-pyrimidinylthio)acetoxy]-milbemycin A₄;

K-77. 13-[(2R)-3-Methyl-2-(2-pyrimidinylthio)butyryloxy]milbemycin A₄;

K-78. 13-[(2S)-3-Methyl-2-(2-pyrimidinylthio)butyryloxy]milbemycin A₄;

and salts thereof.

The compounds of the present invention can be prepared by a variety of processes which are known per se for the preparation of compounds of this type. For example, in general terms, they may be prepared by reducing a compound of formula (VI):

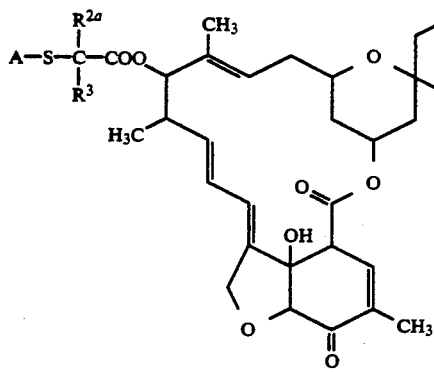

(wherein $R^1$, $R^3$ and A are as defined above, and $R^{2a}$ represents any of the groups or atoms represented by $R^2$ except that any amino-substituted phenyl group is replaced by a nitro-substituted phenyl group), to give a compound of formula (Ia):

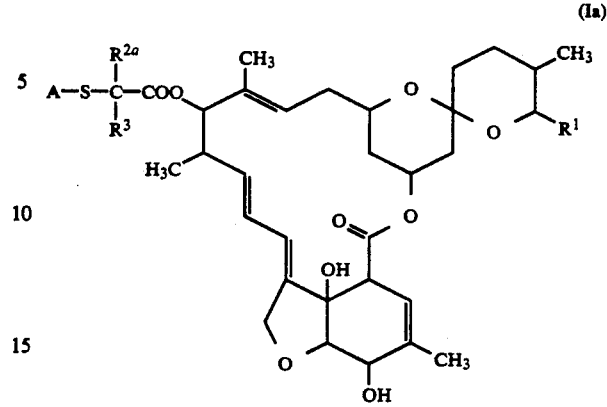

(wherein $R^1$, $R^{2a}$, $R^3$ and A are as defined above), and, where $R^{2a}$ represents a nitro-substituted phenyl group, reducing the compound of formula (Ia), to give a compound of formula (I) in which $R^2$ represents an amino-substituted phenyl group, and optionally salifying the resulting compound.

In more detail, the compounds of the present invention may be prepared as illustrated by the following Reaction Scheme A:

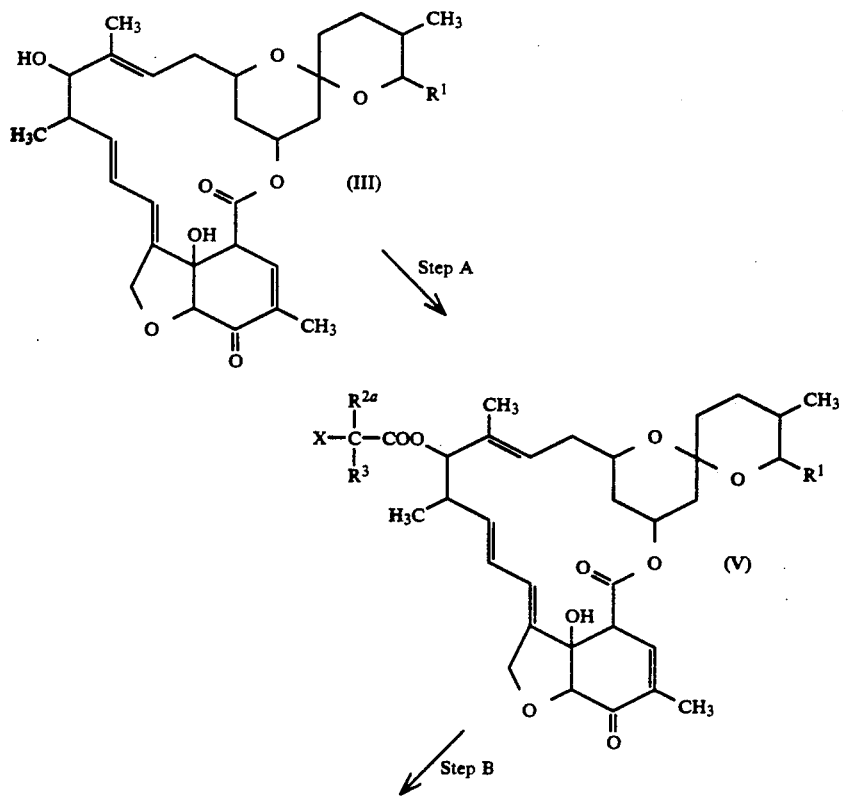

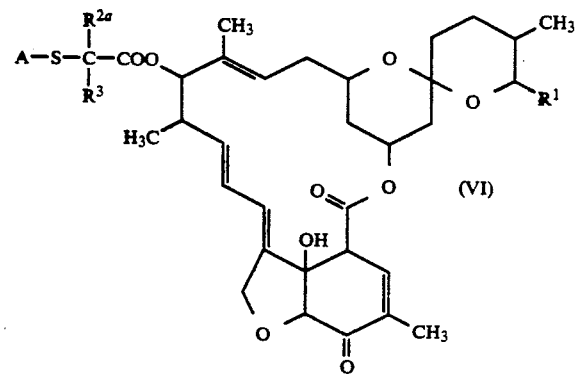

(VI)

Step C

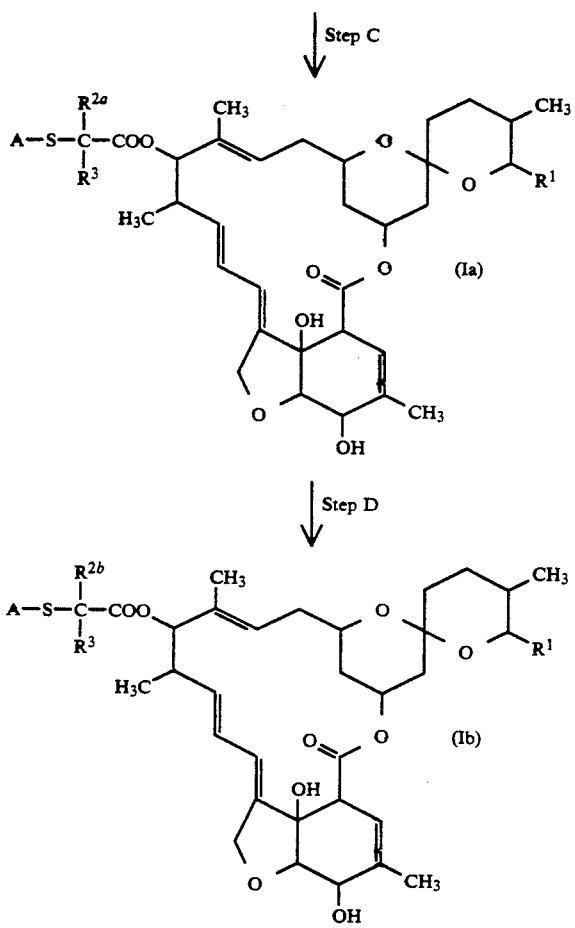

In the above formulae, $R^1$, $R^{2a}$, $R^3$ and A are as defined above, and X represents a halogen atom (for example a chlorine or bromine atom) or a sulfonyloxy group (for example a methanesulfonyloxy group).

Compounds of formula (III), which are amongst the starting materials for use in this Reaction Scheme, can be prepared by the procedure described in Japanese Patent Kokai Application No. Sho 61-103884, that is, by converting a hydroxy group at the 5-position of a corresponding milbemycin to an oxo group and then by hydroxylating the methylene group at the 13-position.

In Step A of this Reaction Scheme, a compound of formula (III) is allowed to react with a carboxylic acid of formula (IV) or with a reactive derivative thereof, to prepare a 13-ester compound of formula (V).

$$X-CR^3(R^{2a})COOH \qquad (IV)$$

(in which $R^{2a}$, $R^3$ and X are as defined above).

Step A consists of a conventional type of esterification reaction between the hydroxy group at the 13-position of the compound of formula (III) and a carboxylic acid of formula (IV), and, hence, it can be carried out by per se well known esterification methods using a carboxylic acid of formula (IV) or a reactive derivative thereof. Examples of reactive derivatives of the carboxylic acid include: acid halides (such as the acid chlorides, acid bromides and acid iodides), acid anhydrides, mixed acid anhydrides, active esters (such as the p-nitrobenzyl ester), reactive amides and any other compounds conventionally used for esterification reactions.

Where a carboxylic acid of formula (IV) itself is used, the reaction is preferably carried out in the presence of a dehydrating agent such as dicyclohexylcarbodiimide (DCC), 2-chloro-1-methylpyridinium iodide, p-toluenesulfonic acid or sulfuric acid.

Where an acid halide of the carboxylic acid of formula (IV) is used, the reaction is preferably carried out in the presence of a base. There is no particular restriction on the nature of the base employed, provided that it has no adverse effect on any part of the molecules of the reagents, and examples of preferred bases include: organic bases, such as triethylamine, N,N-dimethylaniline, pyridine, 4-dimethylaminopyridine, 1,5-diazabicyclo[4.3.0]non-5-ene (DBN) and 1,8-diazabicyclo[5.4.0]undec-7-ene (DBU); and inorganic bases such as sodium hydrogencarbonate, potassium carbonate and sodium hydroxide.

The amount of the acid halide of the carboxylic acid of formula (IV) used is not particularly critical, and is usually within the range of from 1 to 10 equivalents per equivalent of the compound of formula (III), and that of the base used is usually within the range of from 2 to 8 equivalents.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as hexane, petroleum ether, benzene, toluene and xylene; halogenated hydrocarbons, such as chloroform, methylene chloride and o-chlorobenzene; ethers, such as diethyl ether, tetrahydrofuran, dioxane and ethylene glycol dimethyl ether; and esters, such as methyl acetate and ethyl acetate.

The reaction can take place over a wide range of temperatures, and the precise reaction temperature is not critical to the invention. In general, we find it convenient to carry out the reaction at a temperature of from 0° C. to 100° C., more preferably from 20° C. to 50° C. The time required for the reaction may also vary widely, depending on many factors, notably the reaction temperature and the nature of the reagents and solvent employed. However, provided that the reaction is effected under the preferred conditions outlined above, a period of from 30 minutes to 3 hours will usually suffice.

The reactions involving other reactive derivatives are carried out under generally similar conditions or under other conditions, as is well known in the art for esterification reactions.

In Step B of Reaction Scheme A, the group or atom represented by X (X may represent, for example, a chlorine atom, a bromine atom or a methanesulfonyloxy group) at the α-position of the ester moiety at the 13-position in the compound formula (V) is replaced by a group of formula A-S- (in which A is as defined above) by reacting the compound of formula (V) with a thiol compound of formula A-SH in the presence of a base.

There is no particular restriction on the nature of the base employed, provided that it has no adverse effect on any part of the molecules of the reagents, and examples of preferred bases which may be used in this step include: organic tertiary amines, such as triethylamine, tributylamine, diethylisopropylamine, pyridine, 1,4-diazabicyclo[2.2.0]octane and 1,8-diazabicyclo[5.4.0]undec-7-ene (DBU); metal hydrides, including alkali metal and alkaline earth metal hydrides, such as sodium hydride and calcium hydride; alkali metals, such as sodium and lithium; alkyl-alkali metals, such as butyllithium; alkali metal amides, such as lithium diisopropylamide and lithium bis(trimethylsilyl)amide; alkali metal alkoxides, such as sodium methoxide and potassium t-butoxide; and other inorganic bases, especially alkali metal carbonates and hydrogencarbonates, such as sodium hydroxide, potassium hydroxide, sodium carbonate, potassium carbonate and sodium hydrogencarbonate.

The amount of the base used is not particularly critical, and is normally from 1 to 20 equivalents, more preferably 1 to 5 equivalents, per equivalent of the compound of formula (V).

The reaction can take place over a wide range of temperatures; the precise reaction temperature is not critical to the invention, and it can vary widely, depending upon the nature of the base and the reactivity of the compound of formula (V) and the thiol compound used. In general, we find it convenient to carry out the reaction at a temperature of from −70° C. to 90° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours will usually suffice.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as hexane, petroleum ether, benzene and toluene; halogenated hydrocarbons, especially halogenated aliphatic hydrocarbons, such as chloroform and methylene chloride; ethers, such as diethyl ether and tetrahydrofuran; amides, such as dimethylformamide; sulfoxides, such as dimethyl sulfoxide; nitriles, such as acetonitrile; and mixtures of any two or more of the above solvents.

In Step C of Reaction Scheme A, the carbonyl group at the 5-position of the compound of formula (VI) is reduced to a hydroxy group by reacting the compound of formula (VI) with a reducing agent, to give a compound of formula (Ia).

There is no particular limitation upon the nature of the reducing agent used, provided that it is capable of reducting a carbonyl group and provided that other functional groups of the compound of formula (VI) are not affected. Examples of such reducing agents include: reducing agents which function by means of a hydrogen anion, such as sodium borohydride or diborane, preferably sodium borohydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Where the reducing agent used is sodium borohydride, examples of particularly preferred solvents include lower alcohols, such as methanol, ethanol or propanol.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 2 hours will usually suffice.

In Step D of Reaction Scheme A, a compound of formula (Ib), wherein $R^{2b}$ represents a phenyl group substituted with an amino group, can be prepared by reducing the nitro group of a compound of formula (Ia), wherein $R^{2a}$ represents a phenyl group substituted with a nitro group. The reduction of the nitro group can be carried out by conventional means.

One example of such a reduction reaction is catalytic reduction using a noble metal catalyst in the presence of gaseous hydrogen. Examples of preferred catalysts which may be used in this reaction include: palladium on charcoal, palladium on barium sulfate, platinum oxide and the like.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; ethers, such as tetrahydrofuran or dioxane; and esters, such as ethyl acetate.

The reaction can take place over a wide range of temperatures, and the precise reaction temperature is not critical to the invention. In general, we find it convenient to carry out the reaction at a temperature of from 10° C. to 80° C. The time required for the reaction may also vary widely, depending on many factors, notably the reaction temperature and the nature of the reagents and solvent employed. However, provided that the reaction is effected under the preferred conditions outlined above, a period of from 10 minutes to 5 hours will usually suffice.

As another example of a preferred reduction reaction, reduction can be conducted by means of zinc powder in the presence of acetic acid.

This reaction can take place over a wide range of temperatures, and the precise reaction temperature is not critical to the invention. In general, we find it convenient to carry out the reaction at a temperature of from 0° C. to about room temperature. The time required for the reaction may also vary widely, depending on many factors, notably the reaction temperature and the nature of the reagents and solvent employed. However, provided that the reaction is effected under the preferred conditions outlined above, a period of from 30 minutes to 12 hours will usually suffice.

As an alternative to the reactions shown in Reaction Scheme A, the compounds of formula (V) can also be prepared by the procedure summarized in the following Reaction Scheme B:

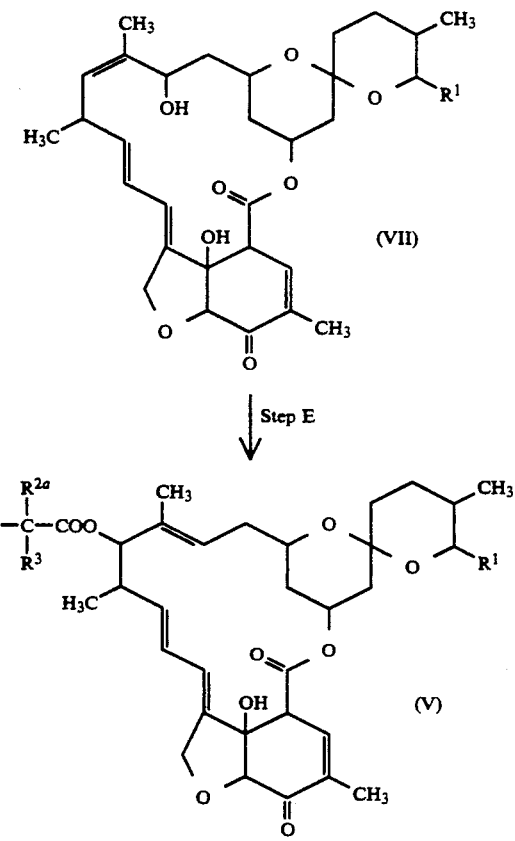

In the above formulae, $R^1$, $R^{2a}$, $R^3$ and A are as defined above.

A 15-hydroxymilbemycin derivative of formula (VII), which is the starting material for this Reaction Scheme, can be prepared by the method described in Japanese Patent Kokai Application Sho 60-158191, the disclosure of which is incorporated herein by reference.

Step E of this Reaction Scheme can be carried out by allowing the compound of formula (VII) to react with a carboxylic acid of formula (IV) in the presence of an acid which serves as catalyst.

There is no particular restriction on the nature of the acid employed as catalyst, and any acid commonly used in reactions of this type may equally be used here, including both inorganic acids and organic acids, for example, hydrochloric acid, sulfuric acid, trifluoroacetic acid, trichloroacetic acid, trifluoromethanesulfonic acid, methanesulfonic acid, p-toluenesulfonic acid, p-nitrobenzenesulfonic acid or benzenesulfonic acid, of which we prefer sulfuric acid, trifluoromethanesulfonic acid, methanesulfonic acid or p-nitrobenzenesulfonic acid.

The amount of acid employed is generally a catalytic amount, and it is therefore enough to use 1 equivalent or less per equivalent of the compound of formula (VII). However, the amount may be varied greatly, depending upon the reactivity of the acid employed, and amounts ranging from a catalytic amount to 5 equivalents may commonly be used.

Furthermore, if a powder of an inorganic compound is added to the reaction system, the reaction is sometimes accelerated, and this may thus also be preferred. Examples of suitable inorganic compounds which may be used, if desired, include copper trifluoromethanesulfonate, cuprous iodide, zinc iodide, cobalt iodide and nickel iodide, of which we prefer to use a copper salt, such as copper trifluoromethanesulfonate or cuprous iodide, and most prefer copper trifluoromethanesulfonate or cuprous iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent; even the carboxylic acid of formula (IV) itself can be used to serve as solvent. Examples of other suitable solvents include: aromatic hydrocarbons, such as benzene, toluene and xylene; halogenated hydrocarbons, especially halogenated aliphatic hydrocarbons, such as methylene chloride, 1,2-dichloroethane and chloroform; esters, such as ethyl acetate and propyl acetate; ethers, such as diethyl ether, tetrahydrofuran, dioxane and dimethoxyethane; amides, such as dimethylformamide, dimethylacetamide and hexamethylphosphoric triamide; sulfoxides, such as dimethyl sulfoxide; and nitriles, such as acetonitrile.

The reaction can take place over a wide range of temperatures, and the precise reaction temperature is not critical to the invention. In general, we find it convenient to carry out the reaction at a temperature of from −10° C. to 100° C., more preferably at from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 6 hours, more preferably from 10 minutes to 2 hours, will usually suffice.

Alternatively, a compound of formula (VI) can be prepared by the process shown in the following Reaction Scheme C:

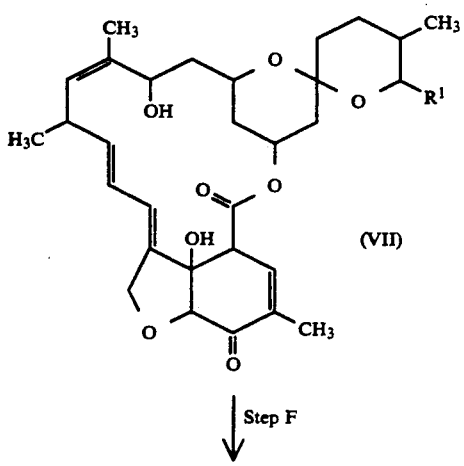

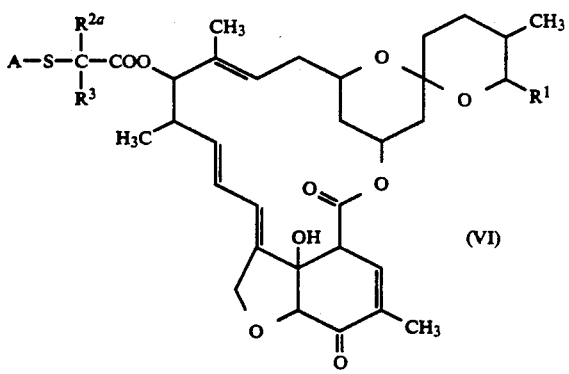

Step F of Reaction Scheme C is carried out by allowing a compound of formula (VII) to react with a carboxylic acid of formula (VIII) in the presence of an acid which serves as catalyst:

(in which $R^{2a}$, $R^3$ and A are as defined above).

There is no particular restriction on the nature of the acid employed as catalyst, and any acid commonly used in reactions of this type may equally be used here, including both inorganic acids and organic acids, for example, hydrochloric acid, sulfuric acid, trifluoroacetic acid, trichloroacetic acid, trifluoromethanesulfonic acid, methanesulfonic acid, p-toluenesulfonic acid, p-nitrobenzenesulfonic acid or benzenesulfonic acid, of which we prefer sulfuric acid, trifluoromethanesulfonic acid, methanesulfonic acid or p-nitrobenzenesulfonic acid.

The amount of acid employed is generally a catalytic amount, and it is therefore enough to use 1 equivalent or less per equivalent of the compound of formula (VII). However, the amount may be varied greatly, depending upon the reactivity of the acid employed, and amounts ranging from a catalytic amount to 5 equivalents may commonly be used.

This reaction may be accelerated by adding a powdery inorganic compound to the reaction system, and this may therefore sometimes be preferred. Examples of such inorganic compounds include: metal salts, such as copper trifluoromethanesulfonate, cuprous iodide, zinc iodide, cobalt iodide or nickel iodide; Celite (trade mark); silica gel; alumina and the like; of these, we prefer the copper salts, such as copper trifluoromethanesulfonate and cuprous iodide; and most preferably copper trifluoromethanesulfonate or cuprous iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Under certain circumstances, the carboxylic acid of formula (VIII) itself can serve as the solvent for this reaction. Examples of other suitable solvents include: aromatic hydrocarbons, such as benzene, toluene and xylene; halogenated hydrocarbons, especially halogenated aliphatic hydrocarbons, such as methylene chloride, 1,2-dichloroethane and chloroform; esters, such as ethyl acetate and propyl acetate; ethers, such as diethyl ether, tetrahydrofuran, dioxane and dimethoxyethane; amides, such as dimethylformamide, dimethylacetamide and hexamethylphosphoric triamide; sulfoxides, such as dimethyl sulfoxide; and nitriles, such as acetonitrile.

The reaction can take place over a wide range of temperatures, and the precise reaction temperature is not critical to the invention. In general, we find it convenient to carry out the reaction at a temperature of from −10° C. to 100° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 6 hours, more preferably from 10 minutes to 2 hours, will usually suffice.

After completion of the reaction, the desired compounds of formulae (V), (VI), (Ia) and (Ib) can be recovered from the reaction mixture by conventional means. The product thus obtained can, if necessary, be further purified by such conventional means the various chromatography techniques, notably column chromatography.

The milbemycins and analogous natural products, which may be used as the starting materials for the synthesis of the compounds of formula (III) or (VII), are generally obtained as mixtures at various ratios of related compounds, and they may be reacted after being separated into the various fractions or they may be used in the above reactions as mixtures, whether the natural mixture or an artificially produced mixture. Therefore, the compound used in each step of the above reactions may be either a single compound or a mixture of compounds. Accordingly, the compound of formula (I) may be prepared as a single compound or as a mixture of compounds, and, if prepared as a mixture of compounds, may be used as such or may be separated into the individual compounds prior to use.

The compounds of the invention have a strong acaricidal activity against adults and eggs of red spiders belonging to the families Tetranychidae, Eriophyidae and the like, which are parasitic to fruit trees, vegetables and flowers. They are also active against mites of the families Ixodidae, Dermanyssidae, Sarcoptidae and the like, which are parasitic to amimals. Further, they are active against resistant mites, which are difficult to control with known acaricides and which have recently caused much trouble.

The compounds of the invention also have a strong insecticidal activity and can therefore be used as insecticides. The active compounds of the invention exhibit precise preventive effects against noxious insects but have no phytotoxicity, and so agricultural plants are never damaged by these compounds. The compounds of the invention can be used to exterminate a variety of noxious insects, including noxious insects which damage plants by sucking or eating them, noxious insects parasitic to plants, noxious insects which damage materials in store, noxious insects for sanitary reasons and the like.

Examples of noxious insects which are susceptible to the compounds of the present invention include: insects of the orders: Coleoptera, for example, *Callosobruchus chinensis, Sitophilus zeamais, Tribolium castaneum, Epilachna vigitioctomaculata, Agriotes fuscicollis, Anomala rufocuprea, Leptinotarsa decemkineata,* Diabrotica spp., *Monochamus alternatus, Lissorhoptrus oxyzophilus* and *Lyctus bruneus*; Lepidoptera, for example, *Lymantria dispar, Malacosoma neustria, Pieris rapae, Spodoptera litura, Mamestra brassicae, Chilo suppressalis, Pyrausta nubilalis, Ephestia cautella, Adoxophyes orana, Carpocapsa pomonella, Agrotis fucosa, Galleria mellonella, Plutella mylostella* and *Phyllocnistis citrella*; Hemiptera, for example, *Nephotettix cincticeps, Nilaparvata lugens, Pseudococcus comstocki, Unaspis vanonensis, Myzus persicae, Aphis pomi, Aphis gossypii, Rhopalosiphum pseudobrassicas, Stephanitis nashi,* Nazara spp., *Cimex lectularius, Trialeurodes vaporariorum* and Psylla spp.; Orthoptera, for example, *Blatella germanica, Periplaneta americana, Gryllotalpa africana* and *Locusta migratoria migratoriodes*; Isoptera, for example, *Deucotermes speratus* and *Coptotermes formosanus*; and Diptera, for example, *Musca domestica, Aedes aegypti, Hylemia platura, Culex pipiens, Anopheles slnensis* and *Culex tritaeniorhynchus.*

Moreover, in the field of veterinary medicine, the compounds of the invention are effective against various animal helminths (both endo- and ectoparasites), for example insects and worms. Examples of noxious animal helminths include: Gastrophilus spp., Stomoxys spp., Trichodectes spp., Rhodnius spp., Trichodectes spp., Rhodnius spp., *Ctenocephalides canis* and the like.

The compounds are also effective against various nematodes which affect animals of agricultural importance. In particular, typical genera of nematodes which are parasitic on livestock, poultry and pet animals, such as pigs, sheep, goats, cows, horses, dogs, cats or fowls and against which the compound of the invention are effective include: Haemonchus, Trichostrongylus, Ostertagia, Nematodirus, Cooperia, Ascaris, Bunostomum, Oesophagostomum, Chabertia, Trichuris, Storongylus, Trichonema, Dictyocaulus, Capillaria, Heterakis, Toxocara, Ascaridia, Oxyuris, Ancylostoma, Uncinaria, Toxascaris and Parascaris.

Certain parasitical species of the genera Nematodirus, Cooperia and Oesophagostomum attack the intestines, while certain species of the general Haemonchus and Ostertagia parasitize the stomach, and parasites belonging to the genus Dictyocaulus are found in the lungs. Parasites belonging to families Filariidae and Setariidae are found in the internal tissues and organs, for example, the heart, the blood vessels, the subcutaneous tissues and the lymphatic vessels. The compounds of the invention are active against all these parasites.

The compounds of the invention are also effective against other parasites, such as parasites of the genera Ancylostoma, Necator, Ascaris, Strongyloides, Trichinella, Capillaria, Trichuris and Enterobius.

The compounds are also active against parasites of the genera Wuchereria, Brugia, Onchoceca and Loa of the family Filariidae (which are found in blood, tissues and organs other than the digestive tract and are medically important), parasites of the genus Dracunculus of the family Dracunculidae and endoinestinal parasites of the genera Strongyloides and Trichinell, which especially infest the exointestinal canal.

Where the compounds of the invention are used as anthelmintics in animals, they can be administered orally in the form of a liquid drink. The drink may comprise a solution, suspension or dispersion of the active compound in an appropriate non-toxic solvent or water and in admixture with a suspending agent, such as bentonite, a wetting agent or other excipients. The drink, in general, may also contain an anti-foaming agent. The active compound is normally present in the drink in an amount of from about 0.01 to 0.5% by weight, more preferably from 0.01 to 0.1% by weight.

Compositions can be administered orally in the form of dry solids, preferably in unit dosage form, such as capsules, pills or tablets containing the desired amount of the active compound. These compositions can be prepared by mixing the active compound uniformly with suitable pulverized diluents, fillers, disintegrators and/or binding agents, for example starch, lactose, talc, magnesium stearate and vegetable gum. The weight and contents of the preparation may vary widely, depending upon the nature of the animal to be treated, the degree of infection, the nature of the parasite and the body weight of the animal to be treated.

The compounds can also be administered as an additive to animal feedstuffs, in which case they can be dispersed uniformly in the feedstuffs, used as a top dressing or used in the form of pellets. The content of active compound in the feedstuff is preferably from 0.0001 to 0.02%, in order to achieve the desired anthelmintic activity.

The compounds of the invention, when dissolved or dispersed in a liquid vehicle, can be administered parenterally to animals by injection into the proventriculus, a muscle or the traches or by subcutaneous injection. For parenteral administration, the active compound is preferably mixed with suitable vegetable oil, such as peanut oil or cottonseed oil. The content of the active compound in the formulation is generally from 0.05 to 50% by weight.

The compounds of the invention can also be administered topically in admixture with a suitable carrier, such as dimethyl sulfoxide or a hydrocarbon solvent. Such preparations are applied directly to the outside of the animal by spraying or by dipping.

The dose of the active compound may vary, depending upon the nature of the animal to be treated, and the nature and degree of parasitic infection. However, best results for oral administration are achieved when the dose is from about 0.01 to 100 mg, more preferably from 0.5 to 50 mg, per 1 kg body wieght. The compound can be administered in a single dose or in divided doses for a relatively short period, such as from 1 to 5 days.

Where the composition of the invention is intended for agricultural or horticultural use, a variety of forms and formulations are possible. For example, it can be formulated as dusts, coarse dusts, soluble powders, microgranules, fine microgranules, wettable powders, dilute emulsions, emusifiable concentrates, aqueous or oily suspensions or aqueous or oily solutions (which can be directly sprayable or can be used for dilution), aerosols or capsules in polymeric substances. The carrier used can be natural or synthetic and organic or inorganic, and it is generally employed to assist the active compound to reach the substrate to be treated, and to make it easier to store, transport or handle the active compound. Solid, liquid and gaseous carriers can be chosen from carriers well known in the art for use with composition of this type.

Such formulations may be prepared by conventional means, e.g. by intimate mixing and/or grinding of the active ingredient(s) with a carrier or diluent (solvent) or, optionally, surface-active agent.

Examples of suitable solvents include: aromatic hydrocarbons, particularly $C_8$ to $C_{12}$ fractions from petroleum distillation, such as xylene mixtures or substituted naphthalenes; esters of phthalic acid, such as dibutyl or dioctyl phthalate; aliphatic or alicyclic hydrocarbons, such as cyclohexane or paraffins; alcohols, such as ethanol, ethylene glycol, ethylene glycol monomethyl ether or ethylene glycol monoethyl ether; glycols or ethers thereof; ketones, such as cyclohexanone; polar solvents, such as N-methyl-2-pyrrolidone, dimethyl sulfoxide or dimethylformamide; optionally epoxidized vegetable oils, such as epoxidized coconut oil or soybean oil; and water.

Examples of carriers which may be used, for example, in dusts and dispersible powders include: natural mineral fillers, such as calcite, talc, kaolin, montmorillonite or attapulgite. In order to improve the physical properties of the composition, it is also possible to add highly dispersed silicic acid or highly dispersed absorbent polymers. Examples of suitable granulated adsorptive carriers include: porous substances, such as pumice, group brick, sepiolite and bentonite; and non-porous substances, such as calcite and sand. A wide variety of pregranulated materials, organic and inorganic, can be used: examples include dolomite and ground plant residues.

As surface-active agents can be used cationic, anionic and non-ionic compound having good emulsifying, dispersing and wetting properties, which are conventionally used. A single such agent or mixtures of such agents can also be used.

Compositions can also contain one or more additives selected from the group consisting of stabilizers, antifoaming agents, viscosity regulators, binders and adhesives or any combination thereof, as well as fertilizers and other active substances to achieve special effects.

Insecticidal and acaricidal compositions generally contain: from 0.01 to 99%, more preferably from 0.1 to 95%, of the active compound; from 1 to 99.99% of a solid or liquid additive; and from 0 to 25%, more preferably from 0.1 to 25%, of a surface-active agent. Where commercial products are generally sold as concentrated compositions, they are generally diluted by the end-user to a concentration of from 0.001 to 0.0001% by weight (from 10 to 1 ppm).

In the above, percentages are by weight.

The compounds of the present invention can be formulated in admixture with or used in association with other active compounds, for example, insecticides, poisonous feeds, bacteriocides, acaricides, nematocides, fungicides, plant growth regulators or herbicides. Examples of the said insecticides include: organic phosphorus chemicals, carbamate chemicals, carboxylate chemicals, chlorinated hydrocarbon chemicals and insecticidal substances produced by microorganism.

The compounds of the invention can also be formulated in admixture with or used in association with synergists. It is required that preparations of such chemicals and the form of the intended use are commercially useful. The synergist is, independently of the activity, in itself a compound capable of enhancing the effect of the active compounds.

The invention is further illustrated by the following non-limiting Examples, which illustrate the preparation of certain of the compounds of the present invention and the preparation of some agrochemical formulations containing the compounds of the present invention. In these Examples, the "Steps" referred to relate to the Steps of the foregoing Reaction Scheme. The compounds of the present invention are also identified by the numbers assigned to them in the foregoing Table 1.

EXAMPLE 1 - (STEP A)

13-(2-Bromo-2-phenylacetoxy)-5-ketomilbemycin A₄
[(V): $R^1$=ethyl, $R^{2a}$=phenyl, $R^3$=hydrogen,
X=bromine]

0.75 ml (9.3 mmole) of pyridine was added to a solution of 3.5 mg (6.3 mmole) of 13-hydroxy-5-ketomilbemycin A₄ in 2 ml of dichloroethane and then 2.93 g (12.6 mmole) of 2-bromo-2-phenylacetyl chloride were added to the mixture. The resulting mixture was then stirred at room temperature for 12 hours. At the end of this time, the reaction mixture was poured into water and extracted with ethyl acetate. The extract was washed with a saturated aqueous solution of sodium chloride and dried over anhydrous sodium sulfate, after which the solvent was removed by distillation under reduced pressure. The resulting residue was then purified by column chromatography through silica gel, using a 3:1 by volume mixture of hexane and ethyl acetate as the eluent, to give 2.41 g (yield 51.0%) of the title compound.

Nuclear Magnetic Resonance Spectrum (CDCl₃, 200 MHz) δ ppm: 6.54 (1H, broad singlet); 5.72–5.90 (2H, multiplet); 4.96 (1H, doublet, J=10.4 Hz); 3.85 (1H, singlet); 3.49–3.68 (2H, multiplet); 3 04 (1H, triplet, J=8.8 Hz).

EXAMPLE 2 - (STEP B)

13-[3-Methyl-2-(5-methyl-2-pyrimidinylthio)butyryloxy]-5-ketomilbemycin A₄ [(VI): $R_1$=ethyl,
$R^{2a}$=isopropyl, $R^3$=hydrogen,
A=5-methyl-2-pyrimidinyl]

7.3 mg (0.087 mmole) of sodium hydrogencarbonate were added to a solution of 33 mg (0.26 mmole) of 5-methylpyrimidine-2-thiol in a mixture of 0.3 ml of water and 0.3 ml of N,N-dimethylformamide, and the resulting mixture was stirred at 80° C. for 40 minutes. After this, the mixture was allowed to cool, and then 50 mg (0.07 mmole) of 13-(2-bromo-3-methylbutyryloxy)-5-ketomilbemycin A₄ (prepared as described in Example 5) were added, and the mixture was stirred at room temperature for 2 hours. At the end of this time, the reaction mixture was poured into water and extracted with ethyl acetate. The extract was washed with a saturated aqueous solution of sodium chloride and dried over anhydrous magnesium sulfate. The solvent was then removed by distillation under reduced pressure. The resulting residue was purified by column chromatography through silica gel, using a stepwise gradient elution method with mixtures of hexane and ethyl acetate ranging from 3:1 to 1:1 by volume as the eluent, to give 84 mg (yield 79%) of the title compound.

Nuclear Magnetic Resonance Spectrum (CDCl₃, 200 MHz) δ ppm: 6.54 (1H, multiplet); 5.74–5.91 (2H, multiplet); 4.97 and 4.96 (together 1H, each doublet, J=10.6 Hz); 4.75 (2H, broad singlet); 4.10 (1H, broad singlet); 3.86 (1H, singlet); 3.50–3.68 (2H, multiplet).

EXAMPLE 3 - (STEP C)

13-[3-Methyl-2-(5-methyl-2-pyrimidinylthio)butyryloxy]milbemycin A₄ (Compound No. K-21) [(Ia):
$R^1$=ethyl, $R^{2a}$=isopropyl, $R^3$=hydrogen,
A=5-methyl-2-pyrimidinyl]

8.4 mg (0.22 mmole) of sodium borohydride were added to a solution of 84 mg (0.11 mmole) of 13-[-3-methyl-2-(5-methyl-2-pyrimiidinylthio)butyryloxy]-5-ketomilbemycin A₄ (prepared as described in Example 2) in 4 ml of methanol, and the resulting mixture was stirred at room temperature for 30 minutes. At the end of this time, the reaction mixture was poured into water and extracted with ethyl acetate. The extract was washed with a saturated aqueous solution of sodium chloride and dried over anhydrous magnesium sulfate. The solvent was then removed by distillation under reduced pressure. The resulting residue was purified by column chromatography through silica gel, using a stepwise gradient elution method with mixtures of hexane and ethyl acetate ranging from 7:3 to 1:1 by volume as the eluent, to give 69 mg (yield 82%) of the title compound.

Mass spectrum (m/z): 766 (M+), 540, 522, 504, 412.
Nuclear Magnetic Resonance Spectrum (CDCl₃, 200 MHz) δ ppm: 4.97 and 4.96 (together 1H, each doublet, J=10.6 Hz); 4.68 (2H, broad singlet); 4.29 (1H, doublet, J=6.0 Hz); 3.95 (1H, doublet, J=6.0 Hz).

EXAMPLE 4 - (STEP D)

13-[2-(4-Aminophenyl)-2-(2-pyrimidinylthio)acetoxy]-milbemycin A₄ (Compound No. K-12) [(Ib): $R^1$=ethyl,
$R^{2b}$=4-aminophenyl, $R^3$=hydrogen,
A=2-pyrimidinyl]

18.5 mg of zinc powder were added to a solution of 25 mg (0.03 mmole) of 13-[2-(4-nitrophenyl)-2-(2-pyrimidinylthio)acetoxy]milbemycin A₄ (prepared in a similar manner to that described in Examples 1 to 3) in 1 ml of a 90% w/v aqueous solution of acetic acid, whilst ice-cooling, and the resulting mixture was stirred for 10 hours. At the end of this time, the reaction mixture was diluted with ethyl acetate, and insoluble materials were filtered off. The filtrate was mixed with water, and the mixture was extracted with ethyl acetate. The extract was washed with a saturated aqueous solution of sodium chloride and dried over anhydrous sodium sulfate; the solvent was then removed by distillation under reduced pressure. The resulting residue was purified by column chromatography through silica gel, using a stepwise gradient elution method with mixtures of hexane and ethyl acetate ranging from 1:3 to 100% hexane as the eluent, to give 14 mg (yield 58%) of the title compound.

Mass spectrum (m/z): 760 (M+ −41), 731, 690, 651.
Nuclear Magnetic Resonance Spectrum (CDCl₃, 200 MHz) δ ppm: 5.78–5.86 (2H, multiplet); 5.22–5.38 (4H, multiplet); 4.95 and 4.93 (together 1H, each doublet, J=10.0 Hz); 4.29 (1H, doublet, J=5.2 Hz); 3.95 (1H, doublet, J=6.4 Hz).

EXAMPLE 5 - (STEP E)

13-(2-Bromo-3-methylbutyryloxy)-5-ketomilbemycin
A₄ [(V): $R^1$=ethyl, $R^{2a}$=isopropyl, $R^3$=hydrogen,
X=bromine]

3 drops of trifluoromethanesulfonic acid were added at room temperature and under a stream of argon to a solution of 315 mg (0.666 mmole) of 15-hydroxy-5-ketomilbemycin A₄ and 510 mg (2.82 mmole) of 2-bromo-3-methylbutyric acid in 6.3 ml of methylene chloride, and the resulting mixture was stirred for 1 hour. At the end of this time, the reaction mixture was poured into water and the mixture was extracted with ethyl acetate. The extract was washed with a 4% w/v aqueous solution of sodium hydrogencarbonate and with a saturated aqueous solution of sodium chloride, in that order, after which it was dried over anhydrous magnesium sulfate; the solvent was then removed by distillation under reduced pressure. The resulting residue was purified by column chromatography through silica gel, using a 7:3 by volume mixture of hexane and ethyl acetate as the eluent, to give 288 mg (yield 71%) of the title compound.

Nuclear Magnetic Resonance Spectrum (CDCl$_3$, 270 MHz) δ ppm: 5.80–5.93 (2H, multiplet); 5.32–5.49 (4H, multiplet);

4.98 and 4.97 (together 1H, each doublet, J=10.5 Hz); 4.72 and 4.78 (2H, AB-quartet, J=14.9 Hz); 4.03 and 4.00 (together 1H, each doublet, J=8.0 Hz); 3.86 (1H, singlet); 3.51–3.66 (2H, multiplet).

EXAMPLE 6 - (STEP F)

13-[-1-(2-Pyrimidinylthio)cyclopentanecarboxy]-5-ketomilbemycin A$_4$ [(VI): R$^1$=ethyl, R$^{2a}$+R$^3$=—(CH$_2$)$_4$—, A=2-pyrimidinyl]

68.1 mg (0.358 mmole) of cuprous iodide, followed by 79.1 μl (0.895 mmole) of trifluoromethanesulfonic acid, were added at room temperature and under a stream of argon gas to 10 ml of a methylene chloride solution containing 100 mg (0.179 mmole) of 15-hydroxy-5-ketomilbemycin A$_4$ and 200 mg (0.895 mmole) of 1-(2-pyrimidinylthio)cyclopentanecarboxylic acid. The mixture was then stirred for 1 hour at room temperature. At the end of this time, the reaction solution was poured into water and extracted with ethyl acetate. The extract was washed with a 4% w/v aqueous solution of sodium hydrogencarbonate and with a saturated aqueous solution of sodium chloride, in that order. The resulting mixture was then dried over anhydrous magnesium sulfate, and the solvent was removed by distillation under reduced pressure. The residue was purified by silica gel column chromatography, using a gradient elution method, with mixtures of hexane and ethyl acetate ranging from 10:1 to 1:1 by volume as the eluent, to obtain 94.5 mg (yield 69.1%) of the title compound.

Mass spectrum (m/z): 762 (M+), 538, 520.

Nuclear Magnetic Resonance Spectrum (CDCl$_3$, 200 MHz) δ ppm: 8.60 (2H, doublet, J=5.1 Hz): 6.92 (1H, triplet, J=1 Hz); 6.54 (1H, triplet, J=1.9 Hz); 5.70–5.90 (2H, multiplet); 5.26–5.46 (3H, multiplet); 4.93 (1H, doublet, J=10.6 Hz); 3.83 (1H, singlet).

EXAMPLE 7 - (STEP E)

13-[(2S)-2-Methanesulfonyloxy-2-phenylacetoxy]-5-ketomilbemycin A$_4$ [(V): R$^1$=ethyl, R$^{2a}$=(S)-phenyl, R$^3$=hydrogen, X=methanesulfonyloxy]

3 drops of trifluoromethanesulfonic acid were added at room temperature and under a stream of argon gas to 6.0 ml of a methylene chloride solution containing 300 mg (0.54 mmole) of 15-hydroxy-5-ketomilbemycin A$_4$ and 503 mg (2.18 mmole) of (2S)-2-methanesulfonyloxy-2-phenylacetic acid. The mixture was then stirred for 2 hours at room temperature. At the end of this time, the reaction solution was Poured into water and extracted with ethyl acetate. The extract was washed with a 4% w/v aqueous solution of sodium hydrogencarbonate and then with a saturated aqueous solution of sodium chloride, after which it was dried over anhydrous magnesium sulfate, and the solvent was removed by distillation under reduced pressure. The resulting residue was purified by silica gel column chromatography, using a stepwise gradient elution method with mixtures of hexane and ethyl acetate ranging from 7:3 to 1:1 by volume as the eluent, to obtain 200 mg (yield 48%) of the title compound.

Nuclear Magnetic Resonance Spectrum (CDCl$_3$, 200 MHz) δ ppm: 6.53 (1H, multiplet); 5.70–5.92 (3H, multiplet): 4.95 (1H, doublet, J=10.6 Hz); 3.99 (1H, singlet); 3.84 (1H, singlet).

EXAMPLE 8 - (STEP B)

13-[(2R)-2-Phenyl-2-(2-pyrimidinylthio)acetoxy]-5-ketomilbemycin A$_4$ [(VI): R$^1$=ethyl R$^{2a}$=(R)-phenyl, R$^3$=hydrogen, A=2-pyrimidinyl]

6.6 mg (0.078 mmole) of sodium hydrogencarbonate were added to a mixture of 0.3 ml of water and 0.3 ml of N,N-dimethylformamide containing 17.5 mg (0.16 mmole) of pyrimidine-2-thiol. The mixture was then stirred for 10 minutes at room temperature, after which 0.3 ml of an N,N-dimethylformamide solution containing 30 mg (0.039 mmole) of 13-[(2S)-2-methanesulfonyloxy-2-phenylacetoxy)-5-ketomilbemycin A$_4$ (prepared as described in Example 7) was added to the reaction mixture, and the mixture was stirred for 1 hour at room temperature. At the end of this time, the reaction solution was poured into water and extracted with ethyl acetate. The extract was washed with water and then with a saturated aqueous solution of sodium chloride. It was then dried over anhydrous magnesium sulfate, and the solvent was removed by distillation under reduced pressure. The resulting residue was purified by silica gel column chromatography, using a 7:3 by volume mixture of hexane and ethyl acetate as the eluent, to obtain 13.2 mg (yield 43%) of the title compound.

Nuclear Magnetic Resonance Spectrum (CDCl$_3$, 200 MHz) δ ppm: 6.53 (1H, multiplet); 5.71–5.90 (2H, multiplet); 5.54 (1H, singlet); 4.96 (1H, doublet, J=10.6 Hz); 4.04 (1H, singlet); 3.85 (1H, singlet).

EXAMPLE 9 - (STEP C)

13-[(2R)-2-phenyl-2-(2-pyrimidinylthio)acetoxy]milbemycin A$_4$ (Compound No. K-68) [(Ia): R$^1$=ethyl R$^{2a}$=(R)-phenyl, R$^3$=hydrogen, A=2-pyrimidinyl]

1.3 mg (0.034 mmole) of sodium borohydride were added to 1 ml of a methanol solution containing 13 mg (0.017 mmole) of 13-[(2R)-2-phenyl-2-(2-pyrimidinylthio)acetoxy]-5-ketomilbemycin A$_4$ (prepared as described in Example 8), and the mixture was stirred for 30 minutes at room temperature. At the end of this time, the reaction solution was poured into water and extracted with ethyl acetate. The extract was washed with water and then with a saturated aqueous solution of sodium chloride. It was then dried over anhydrous magnesium sulfate, and the solvent was removed by distillation under reduced pressure. The resulting residue was purified by silica gel column chromatography, using a stepwise gradient elution method with mixtures of hexane and ethyl acetate ranging from 7:3 to 1:1 by volume as the eluent, to obtain 7.2 mg (yield 54%) of the title compound.

Mass spectrum (m/z): 786 (M+), 658, 540, 522, 504.

Nuclear Magnetic Resonance Spectrum (CDCl$_3$, 200 MHz) δ ppm: 5.74–5.85 (2H, multiplet); 5.53 (1H, singlet); 5.25–5.41 (4H, multiplet); 4.96 (1H, doublet, J=10.5 Hz); 4.08 (1H, broad singlet); 3.95 (1H, doublet, J=6.2 Hz).

EXAMPLES 10 TO 99

Following a procedure similar to that described in the above Examples, the compounds of Examples 10 to 99 were synthesized.

In order to illustrate in more detail the procedures employed in the process of the present invention, the Steps used and the yield (%) of each Step are specified after each compound number. The asterisk denotes that the product obtained was used in the subsequent reaction without further purification, and thus its yield was not estimated in that Step.

EXAMPLE 10

13-[2-(2-pyrimidinylthio)butyryloxy]milbemycin $A_4$ [Compound No. K-1: Step E (*) - Step B (61%) - Step C (71%)]

Nuclear Magnetic Resonance Spectrum (CDCl$_3$, 200 MHz) δ ppm: 5.72–5.90 (2H, multiplet); 5.28–5.48 (4H, multiplet); 4.95 and 5.00 (together 1H, each doublet, J=10.5 Hz); 4.06 (1H, singlet); 3.97 (1H, doublet, J=5.8 Hz).

EXAMPLE 11

13-[2-(2-pyrimidinylthio)pentanoyl]milbemycin $A_4$ [Compound No. K-2: Step E (*) - Step B (96%) - Step C (49%)]

Nuclear Magnetic Resonance Spectrum (CDCl$_3$, 200 MHz) δ ppm: 5.72–5.90 (2H, multiplet); 5.29–5.44 (4H, multiplet); 4.94 and 4.99 (together 1H, each doublet, J=10.2 Hz); 4.06 (1H, singlet); 3.97 (1H, doublet, J=5.9 Hz).

EXAMPLE 12

13-[3-Methyl-2-(2-pyrimidinylthio)butyryloxy]milbemycin $A_4$ [Compound No. K-3: Step E(*) - Step B (50%) - Step C (86%)]

Mass spectrum (m/z): 558 (M+ −194), 540, 522.
Nuclear Magnetic Resonance Spectrum (CDCl$_3$, 200 MHz) δ ppm: 5.72–5.90 (2H, multiplet); 5.28–5.46 (4H, multiplet); 4.96 and 5.01 (together 1H, each doublet, J=10.8 Hz); 4.07 (1H, singlet); 3.98 (1H, doublet, J=5.9 Hz).

EXAMPLE 13

13-[2-(2-pyrimidinylthio)hexanoyloxy]milbemycin $A_4$ [Compound No. K-4: Step E (86%) - Step B (100%) - Step C (81%)]

Mass spectrum (m/z): 766 (M+), 637, 540, 522.
Nuclear Magnetic Resonance Spectrum (CDCl$_3$, 200 MHz) δ ppm: 5.79–5.88 (2H, multiplet); 5.26–5.43 (4H, multiplet); 4.98 and 4.93 (together 1H, each doublet, J=10.5 Hz); 4.29 (1H, doublet, J=6.4 Hz); 3.96 (1H, doublet, J=6.5 Hz).

EXAMPLE 14

13-[3-Methyl-2-(2-pyrimidinylthio)pentanoyloxy]milbemycin $A_4$ [Compound No. K-5: Step E (88%) - Step B (49%) - Step C (82%)]

Mass spectrum (m/z): 766 (M+), 540, 522, 488.
Nuclear Magnetic Resonance Spectrum (CDCl$_3$, 200 MHz) δ ppm: 5.72–5.89 (2H, multiplet); 5.26–5.46 (4H, multiplet); 4.99 and 4.96 (together 1H, each doublet, J=10.5 Hz); 4.29 (1H, doublet, J=6.0 Hz); 3.96 (1H, doublet, J=6.4 Hz).

EXAMPLE 15

13-[2-Cyclopentyl-2-(2-pyrimidinylthio)acetoxy]milbemycin $A_4$ [Compound No. K-6: Step E (*) - Step B (63%) - Step C (65%)]

Mass spectrum (m/z): 778 (M+), 760, 540, 522.
Nuclear Magnetic Resonance Spectrum (CDCl$_3$, 200 MHz) δ ppm: 5.71–5.89 (2H, multiplet); 5.23–5.48 (4H, multiplet); 5.00 and 4.95 (together 1H, each doublet, J=10.5 Hz); 4.08 (1H, singlet); 3.97 (1H, doublet, J=5.8 Hz).

EXAMPLE 16

13-[2-Cyclohexyl 2-(2-pyrimidinylthio)acetoxy]milbemycin $A_4$ [Compound No. K-7: Step E (*) - Step B (97%) - Step C (43%)]

Mass spectrum (m/z): 792 (M+), 734, 698, 540.
Nuclear Magnetic Resonance Spectrum (CDCl$_3$, 200 MHz) δ ppm: 5.70–5.99 (2H, multiplet); 5.20–5.44 (4H, multiplet); 4.92 and 4.99 (together 1, each doublet, J=10.7 Hz); 4.19 (1H, singlet); 3.95 (1H, doublet, J=5.8 Hz).

EXAMPLE 17

13-[2-Phenyl-2-(2-pyrimidinylthio)acetoxy]milbemycin $A_4$ [Compound No. K-8: Step A (51%) - Step B (70%) - Step C (60%)]

Mass spectrum (m/z): 559 (M+ −227), 541, 523.
Nuclear Magnetic Resonance Spectrum (CDCl$_3$, 270 MHz) δ ppm: 5.72–5.85 (2H, multiplet); 5.24–5.45 (4H, multiplet); 4.96 and 4.92 (together 1H, each doublet, J=10.5 Hz); 4.08 and 4.05 (together 1H, each singlet); 3.23–3.29 (1H, multiplet).

EXAMPLE 18

13-[2-(2-Methylphenyl)-2-(2-pyrimidinylthio)acetoxy]milbemycin $A_4$ [Compound No. K-9: Step A (51%) - Step B (49%) - Step C (59%)]

Mass spectrum (m/z): 800 (M+), 652, 540.
Nuclear Magnetic Resonance Spectrum (CDCl$_3$, 200 MHz) δ ppm: 5.68–5.84 (2H, multiplet); 5.23–5.48 (4H, multiplet); 4.92 and 4.98 (together 1H, each doublet, J=10.7 Hz); 4.08 (1H, doublet, J=4.8 Hz); 3.96 (1H, doublet, J=5.8 Hz).

EXAMPLE 19

13-[2-(4-Chlorophenyl) 2-(2-pyrimidinylthio)acetoxy]milbemycin $A_4$ [Compound No. K-10: Step E (65%) - Step B (66%) - Step C (81%)]

Mass spectrum (m/z): 820 (M+), 710, 674.
Nuclear Magnetic Resonance Spectrum (CDCl$_3$, 200 MHz) δ ppm: 5.82–5.77 (2H, multiplet); 5.41–5.29 (4H, multiplet); 4.95 and 4.94 (together 1H, each doublet, J=10.7 Hz); 3.96 (1H, doublet, J=5.9 Hz); 3.75–3.45 (1H, multiplet).

EXAMPLE 20

13-[2-(2-Chlorophenyl)-2-(2-pyrimidinylthio)acetoxy]milbemycin $A_4$ [Compound No. K-11: Step A (72%) - Step B (49%) - Step C (62%)]

Mass spectrum (m/z): 711 (M+ −109), 652, 572, 558.
Nuclear Magnetic Resonance Spectrum (CDCl$_3$, 200 MHz) δ ppm: 6.06–6.16 (1H, multiplet); 5.71–5.86 (2H, multiplet); 5.20–5.43 (3H, multiplet); 4.97 and 4.94 (together 1H, each doublet, J=8.5 Hz); 4.28 (1H, doublet, J=5.2 Hz); 3.55 (1H, multiplet); 3.25 (1H, multiplet); 3.03 (1H, multiplet).

EXAMPLE 21

13-[2-(2-Fluorophenyl)-2-(2-pyrimidinylthio)acetoxy]-milbemycin A$_4$ [Compound No. K-13: Step A (77%) - Step B (60%) - Step C (68%)]

Mass spectrum (m/z): 804 (M+), 766.
Nuclear Magnetic Resonance Spectrum (CDCl$_3$, 200 MHz) δ ppm: 5.93 (1H, doublet, J=5.5 Hz); 5.77–5.82 (2H, multiplet); 5.28–5.40 (3H, multiplet); 4.97 and 4.92 (together 1H, each doublet, J=10.3 Hz); 4.08 and 4.07 (together 1H, each singlet); 3.95 (1H, doublet, J=6.2 Hz); 3.43–3.70 (1H, multiplet); 3.24–3.27 (1H, multiplet); 2.95–3.10 (1H, multiplet).

EXAMPLE 22

13-[2-(2-pyrimidinylthio)-2-(2-trifluoromethylphenyl)-acetoxy]milbemycin A$_4$ [Compound No. K-14: Step E (*) - Step B (75%) - Step C (72%)]

Mass spectrum (m/z): 854 (M+), 744, 726, 540.
Nuclear Magnetic Resonance Spectrum (CDCl$_3$, 200 MHz) δ ppm: 5.72–5.83 (2H, multiplet); 5.21–5.42 (4H, multiplet); 4.89 and 4.93 (together 1H, each doublet, J=10.2 Hz); 4.08 (1H, doublet, J=4.3 Hz).

EXAMPLE 23

13-[2-(2,6-Difluorophenyl)-2-(2-pyrimidinylthio)acetoxy]milbemycin A$_4$ [Compound No. K-15: Step E (*) - Step B (94%) - Step C (80%)]

Mass spectrum (m/z): 822 (M+), 724, 688, 583.
Nuclear Magnetic Resonance Spectrum (CDCl$_3$, 200 MHz) δ ppm: 5.68–5.82 (2H, multiplet); 5.27–5.46 (4H, multiplet); 4.92 and 4.99 (together 1H, each doublet, J=14.1 Hz); 4.07 (1H, singlet); 3.95 (1H, doublet, J=5.8 Hz).

EXAMPLE 24

13-[3-Methyl-2-(4-methyl-2-pyrimidinylthio)butyryloxy]milbemycin A$_4$ [Compound No. K-16: Step E (71%) - Step B (38%) - Step C (79%)]

Mass spectrum (m/z): 766 (M+), 736, 706, 540, 522.
Nuclear Magnetic Resonance Spectrum (CDCl$_3$, 200 MHz) δ ppm: 4.97 (1H, doublet, J=10.4 Hz); 4.68 (2H, broad singlet); 4.29 (1H, doublet, J=5.6 Hz); 4.06 (1H, broad singlet); 3.95 (1H, doublet, J=5.6 Hz).

EXAMPLE 25

13-[2-(4-Methyl-2-pyrimidinylthio)-2-phenylacetoxy]-milbemycin A$_4$ [Compound No. K-17: Step E (72%) - Step B (76%) - Step C (68%)]

Mass spectrum (m/z): 800 (M+), 782, 764.
Nuclear Magnetic Resonance Spectrum (CDCl$_3$, 200 MHz) δ ppm: 4.95 and 4.94 (together 1H, each doublet, J=10.5 Hz); 4.05 and 4.04 (together 1H, each singlet); 3.95 (1H, doublet, J=6.2 Hz); 3.65–3.47 (1H, multiplet); 3.28–3.21 (1H, multiplet); 3.10–2.97 (1H, multiplet).

EXAMPLE 26

13-[2-(4-Chlorophenyl)-2-(4-methyl-2-pyrimidinylthio)acetoxy]milbemycin A$_4$ [Compound No. 18: Step E (61%) - Step B (78%) - Step C (65%)]

Mass spectrum (m/z): 834 (M+), 674, 628.
Nuclear Magnetic Resonance Spectrum (CDCl$_3$, 200 MHz) δ ppm: 5.81–5.77 (2H, multiplet); 5.39–5.28 (4H, multiplet); 4.95 and 4.93 (together 1H, each doublet, J=10.6 Hz); 4.28 (1H, doublet, J=5.9 Hz); 4.10–4.00 (1H, broad); 3.95 (1H, doublet, J=6.2 Hz).

EXAMPLE 27

13-[2-(2-Chlorophenyl)-2-(4-methyl-2-pyrimidinylthio)acetoxy]milbemycin A$_4$ [Compound No. K-19: Step A (70%) - Step B (55%) - Step C (88%)]

Mass spectrum (m/z): 834 (M+), 816, 798.
Nuclear Magnetic Resonance Spectrum (CDCl$_3$, 200 MHz) δ ppm: 4.96 (1H, doublet, J=10.3 Hz); 3.95 (1H, doublet, J=6.2 Hz); 3.68–3.43 (1H, multiplet); 3.28–3.21 (1H, multiplet); 3.11–2.95 (1H, multiplet).

EXAMPLE 28

13-[2-(2-Fluorophenyl)-2-(4-methyl-2-pyrimidinylthio)acetoxy]milbemycin A$_4$ [Compound No. K-20: Step A (88%) - Step B (59%) - Step C (60%)]

Mass spectrum (m/z): 540 (M+−278), 505, 412, 279.
Nuclear Magnetic Resonance Spectrum (CDCl$_3$, 200 MHz) δ ppm: 4.95 (1H, doublet, J=10.3 Hz); 4.60–4.70 (2H, multiplet); 4.27 (1H, doublet, J=4.6 Hz); 4.00–4.10 (1H, broad singlet); 3.95 (1H, doublet, J=6.2 Hz); 3.35–3.65 (1H, multiplet); 3.20–3.30 (1H, multiplet); 2.95–3.10 (1H, multiplet).

EXAMPLE 29

13-[2-(5-Methyl-2-pyrimidinylthio)-2-phenylacetoxy]-milbemycin A$_4$ [Compound No. K-22: Step E (72%) - Step B (78%) - Step C (84%)]

Mass spectrum (m/z): 801 (M++1), 783, 765.
Nuclear Magnetic Resonance Spectrum (CDCl$_3$, 200 MHz) δ ppm: 4.94 and 4.92 (together 1H, each doublet, J=10.5 Hz); 4.09 and 4.05 (together 1H, each singlet); 3.95 (1H, doublet, J=6.2 Hz); 3.63–3.43 (1H, multiplet); 3.29–3.21 (1H, multiplet); 3.11–2.95 (1H, multiplet).

EXAMPLE 30

13-[2-(2-Methylphenyl)-2-(5-methyl-2-pyrimidinylthio)acetoxy]milbemycin A$_4$ [Compound No. K-23: Step A (*) - Step B (*) - Step C (12%)]

Mass spectrum (m/z): 814 (M+).
Nuclear Magnetic Resonance Spectrum (CDCl$_3$, 200 MHz) δ ppm: 4.95 (1H, doublet, J=10.5 Hz); 4.10 (1H, singlet); 3.96 (1H, doublet, J=6.2 Hz); 3.70–3.45 (1H, multiplet); 3.28–3.21 (1H, multiplet); 3.10–2.98 (1H, multiplet).

EXAMPLE 31

13-[2-(4-Chlorophenyl)-2-(5-methyl-2-pyrimidinylthio)acetoxy]milbemycin A$_4$ [Compound No. K-24: Step E (61%) - Step B (45%) - Step C (69%)]

Mass spectrum (m/z): 834 (M+), 816, 540.
Nuclear Magnetic Resonance Spectrum (CDCl$_3$, 200 MHz) δ ppm: 5.82–5.77 (2H, multiplet); 5.39–5.28 (4H, multiplet); 4.94 and 4.92 (together 1H, each doublet, J=10.6 Hz); 4.29 (1H, doublet, J=5.2 Hz); 3.95 (1H, doublet, J=6.2 Hz).

EXAMPLE 32

13-[2-(2-Chlorophenyl)-2-(5-methyl-2-pyrimidinylthio)acetoxy]milbemycin A4 [Compound No. K-25: Step A (70%) - Step B (77%) - Step C (79%)]

Mass spectrum (m/z): 834 (M+), 540.
Nuclear Magnetic Resonance Spectrum (CDCl$_3$, 200 MHz) δ ppm: 4.96 and 4.92 (together 1H, each doublet, J=10.5 Hz); 4.29 (1H, doublet, J=5.1 Hz); 3.95 (1H, doublet, J=6.2 Hz); 3.63-3.48 (1H, multiplet); 3.28-3.21 (1H, multiplet); 3.10-2.97 (1H, multiplet).

EXAMPLE 33

13-[2-(2-Fluorophenyl)-2-(5-methyl-2-pyrimidinylthio)acetoxy]milbemycin A4 [Compound No. K-26: Step A (88%) - Step B (47%) - Step C (37%)]

Mass spectrum (m/z): 818 (M+), 800, 704.
Nuclear Magnetic Resonance Spectrum (CDCl$_3$, 200 MHz) δ ppm: 4.98 and 4.91 (together 1H, each doublet, J=5.8 Hz); 4.65-4.70 (2H, multiplet); 4.28 (1H, doublet, J=4.5 Hz); 3.90-4.10 (1H, broad singlet); 3.95 (1H, doublet, J=5.1 Hz); 3.44-3.68 (1H, multiplet); 3.20-3.30 (1H, multiplet); 2.90-3.10 (1H, multiplet).

EXAMPLE 34

13-[2-(4,6-Dimethyl-2-pyrimidinylthio)-3-methylbutyryloxy]milbemycin A4 [Compound No. K-27: Step E (71%) - Step B (*) - Step C (44%)]

Mass spectrum (m/z): 780 (M+), 762, 744, 700.
Nuclear Magnetic Resonance Spectrum (CDCl$_3$, 200 MHz) δ ppm: 5.71-5.89 (2H, multiplet); 5.27-5.44 (4H, multiplet); 4.99 and 4.95 (together 1H, each doublet, J=10.5 Hz); 4.29 (1H, doublet, J=5.8 Hz); 4.08 (1H, broad singlet); 4.03 (1H, broad singlet); 3.96 (1H, doublet, J=5.8 Hz).

EXAMPLE 35

13-[2-(4,6-Dimethyl-2-pyrimidinylthio)-2-phenylacetoxy]milbemycin A4 [Compound No. K-28: Step E (72%) - Step B (78%) - Step C (85%)]

Mass spectrum (m/z): 814 (M+), 676.
Nuclear Magnetic Resonance Spectrum (CDCl$_3$, 200 MHz) δ ppm: 4.90 and 4.85 (together 1H, each doublet, J=10.5 Hz); 3.95 (1H, broad singlet); 3.88 (1H, doublet, J=6.2 Hz); 3.63-3.40 (1H, multiplet); 3.20-3.23 (1H, multiplet); 3.00-2.90 (1H, multiplet).

EXAMPLE 36

13-[2-(4,6-Dimethyl-2-pyrimidinylthio)-2-(2-methylphenyl)acetoxy]milbemycin A4 [Compound No. K-29: Step E (*) - Step B (*) - Step C (8%)]

Mass spectrum (m/z): 828 (M+), 810, 540.
Nuclear Magnetic Resonance Spectrum (CDCl$_3$, 200 MHz) δ ppm: 4.99 and 4.92 (together 1H, each doublet, J=10.6 Hz); 4.03 (1H, broad singlet); 3.94 (1H, doublet, J=6.2 Hz); 3.63-3.47 (1H, multiplet); 3.28-3.22 (1H, multiplet); 3.10-2.97 (1H, multiplet).

EXAMPLE 37

13-[2-(4-Chlorophenyl)-2-(4,6-dimethyl-2-pyrimidinylthio)acetoxy]milbemycin A4 [Compound No. K-30: Step E (61%) - Step B (60%) - Step C (58%)]

Mass spectrum (m/z): 848 (M+), 804, 582.
Nuclear Magnetic Resonance Spectrum (CDCl$_3$, 200 MHz) δ ppm: 5.81-5.76 (2H, multiplet); 5.43-5.28 (4H, multiplet); 4.98 and 4.92 (together 1H, each doublet, J=10.7 Hz); 4.29 (1H, doublet, J=6.0 Hz); 4.04 (1H, broad singlet); 3.95 (1H, doublet, J=6.9 Hz).

EXAMPLE 38

13-[2-(2-Chlorophenyl)-2-(4,6-dimethyl-2-pyrimidinylthio)acetoxy]milbemycin A4 [Compound NO. K-31: Step A (70%) - Step B (71%) - Step C (80%)]

Mass spectrum (m/z): 830 (M+ −18), 810.
Nuclear Magnetic Resonance Spectrum (CDCl$_3$, 200 MHz) δ ppm: 4.97 and 4.93 (together 1H, each doublet, J=10.6 Hz); 4.07 (1H, broad singlet); 4.03 (1H, broad singlet); 3.95 (1H, doublet, J=6.2 Hz); 3.63-3.49 (1H, multiplet); 3.27-3.22 (1H, multiplet); 3.09-2.95 (1H, multiplet).

EXAMPLE 39

13-[2-(4,6-Dimethyl-2-pyrimidinylthio)-2-(2-fluorophenyl)acetoxy]milbemycin A4 [Compound No. K-32: Step A (88%) - Step B (58%) - Step C (77%)]

Mass spectrum (m/z): 706 (M+ −126), 670, 626.
Nuclear Magnetic Resonance Spectrum (CDCl$_3$, 200 MHz) δ ppm: 4.97 and 4.94 (together 1H, each doublet, J=10.5 Hz); 4.50-4.70 (2H, broad singlet); 4.28 (1H, broad doublet, J=5.6 Hz); 4.05 (1H, broad singlet); 3.94 (1H, doublet, J=6.2 Hz); 3.45-3.65 (1H, multiplet); 3.20-3.30 (1H, multiplet); 2.95-3.10 (1H, multiplet).

EXAMPLE 40

13-[2-(5-Chloro-2-pyrimidinylthio)-3-methylbutyryloxy]milbemycin A4 [Compound No. K-33: Step E (71%) - Step B (63%) - Step C (42%)]

Mass spectrum (m/z): 786 (M+), 768, 750, 720, 540.
Nuclear Magnetic Resonance Spectrum (CDCl$_3$, 200 MHz) δ ppm: 4.97 and 4.96 (together 1H, each doublet, J=10.5 Hz); 4.68 (2H, broad singlet); 4.29 (1H, doublet, J=6.1 Hz); 3.95 (1H, doublet, J=6.1 Hz); 3.48-3.66 (1H, multiplet); 3.26 (1H, multiplet); 3.02 (1H, triplet, J=8.8 Hz).

EXAMPLE 41

13-[2-(5-Chloro-2-pyrimidinylthio)-2-phenylacetoxy]milbemycin A4 [Compound No. K-34: Step E (72%) - Step B (79%) - Step C (69%)]

Mass spectrum (m/z): 820 (M+), 802, 692.
Nuclear Magnetic Resonance Spectrum (CDCl$_3$, 200 MHz) δ ppm: 4.94 and 4.92 (together 1H, each doublet, J=10.6 Hz); 4.10 (1H, broad singlet); 4.04 (1H, broad singlet); 3.96 (1H, doublet, J=6.2 Hz); 3.64-3.47 (1H, multiplet); 3.20-3.12 (1H, multiplet); 3.10-2.97 (1H, multiplet).

EXAMPLE 42

13-[2-(4-Chlorophenyl)-(5-chloro-2-pyrimidinylthio)-2-acetoxy]milbemycin A4 [Compound No. K-35: Step E (61%) - Step B (52%) - Step C (50%)]

Mass spectrum (m/z): 709 (M+ −145), 600, 540.
Nuclear Magnetic Resonance Spectrum (CDCl$_3$, 200 MHz) δ ppm: 5.83-5.77 (2H, multiplet); 5.44-5.26 (4H, multiplet); 4.94 and 4.93 (together 1H, each doublet, J=10.0 Hz); 4.68 (2H, singlet); 4.29 (1H, doublet, J=6.3 Hz); 3.95 (1H, doublet, J=6.6 Hz).

EXAMPLE 43

13-[2-(2-Chlorophenyl)-2-(5-chloro-2-pyrimidinylthio)acetoxy]milbemycin A$_4$ [Compound No. K-36: Step A (70%) - Step B (73%) - Step C (64%)]

Mass spectrum (m/z): 854 (M+), 836, 710.
Nuclear Magnetic Resonance Spectrum (CDCl$_3$, 200 MHz) δ ppm: 4.96 and 4.93 (together 1H, each doublet, J=10.6 Hz); 4.05 (1H, broad singlet); 3.96 (1H, doublet, J=6.2 Hz); 3.60–3.47 (1H, multiplet); 3.28–3.21 (1H, multiplet); 3.10–3.00 (1H, multiplet).

EXAMPLE 44

13-[3-Methyl-2-(4-pyrimidinylthio)butyryloxy]milbemycin A$_4$ [Compound No. K-37: Step E (71%) - Step B (38%) - Step C (62%)]

Mass spectrum (m/z): 752 (M+), 723, 540.
Nuclear Magnetic Resonance Spectrum (CDCl$_3$, 200 MHz) δ ppm: 4.98 and 4.97 (together 1H, each doublet, J=10.5 Hz); 4.69 (2H, broad singlet); 4.28 (1H, doublet, J=6.2 Hz); 4.05 (1H, broad singlet); 3.96 (1H, doublet, J=6.2 Hz); 3.48–3.68 (1H, multiplet).

EXAMPLE 45

13-[2-Phenyl-2-(4-pyrimidinylthio)acetoxy]milbemycin A$_4$ [Compound No. K-38: Step A (31%) - Step B (*) - Step C (58%)]

Mass spectrum (m/z): 786 (M+), 768, 750, 692.
Nuclear Magnetic Resonance Spectrum (CDCl$_3$, 200 MHz) δ ppm: 5.75–5.84 (2H, multiplet); 5.24–5.45 (4H, multiplet); 4.92 and 4.98 (together 1H, each doublet, J=10.2 Hz); 3.95 and 3.97 (together 1H, each doublet, J=6.4 Hz).

EXAMPLE 46

13-[3-Methyl 2-(2-pyrazinylthio)butyryloxy]milbemycin A$_4$ [Compound No. K-39: Step E (71%) - Step B (46%) - Step C (43%)]

Mass spectrum (m/z): 752 (M+), 540, 504, 460.
Nuclear Magnetic Resonance Spectrum (CDCl$_3$, 200 MHz) δ ppm: 5.70–5.80 (2H, multiplet); 5.25–5.45 (4H, multiplet); 4.96 and 4.97 (together 1H, each doublet, J=10.5 Hz); 4.68 (2H, broad singlet); 4.29 (1H, doublet, J=5.3 Hz); 4.05 (1H, broad singlet); 3.95 (1H, doublet, J=6.2 Hz); 3.45–3.65 (1H, multiplet); 3.20–3.30 (1H, multiplet); 3.03 (1H, triplet, J=9.5 Hz).

EXAMPLE 47

13-[3-Methyl-2-(2-pyrimidinylthio)butyryloxy]milbemycin A$_3$ [Compound No. K-40: Step E (91%) - Step B (34%) - Step C (76%)]

Mass spectrum (m/z): 739 (M+1), 526, 508, 398.
Nuclear Magnetic Resonance Spectrum (CDCl$_3$, 270 MHz) δ ppm: 5.75–5.82 (2H, multiplet); 5.30–5.38 (4H, multiplet); 4.98 and 4.96 (together 1H, each doublet, J=10.5 Hz); 4.28 (1H, triplet, J=6.5 Hz); 4.06 (1H, doublet, J=1.6 Hz); 3.90 (1H, doublet, J=6.5 Hz).

EXAMPLE 48

13-[2-phenyl-2 (2-pyrimidinylthio)acetoxy]milbemycin A$_3$ [Compound No. K-42: Step E (87%) - Step B (59%) - Step C (90%)]

Mass spectrum (m/z): 773 (M+1), 726, 712, 526.
Nuclear Magnetic Resonance Spectrum (CDCl$_3$, 270 MHz) δ ppm: 5.73–5.80 (2H, multiplet); 5.24–5.41 (4H, multiplet); 4.95 and 4.92 (together 1H, each doublet, J=10.5 Hz); 4.28 (1H, triplet, J=6.4 Hz); 3.95 and 3.94 (together 1H, each doublet, J=6.4 Hz).

EXAMPLE 49

13-[2-phenyl-2-(2-pyrimidinylthio)acetoxy]milbemycin D [Compound No. K-43: Step E (44%) - Step B (*) - Step C (19%)]

Mass spectrum (m/z): 800 (M+), 756, 554, 516.
Nuclear Magnetic Resonance Spectrum (CDCl$_3$, 270 MHz) δ ppm: 5.77–5.80 (2H, multiplet); 5.28–5.38 (4H, multiplet); 4.95 and 4.93 (together 1H, each doublet, J=10.5 Hz); 4.29 (1H, broad singlet); 4.06 (1H, doublet, J=4.4 Hz); 3.97 (doublet, J=6.5 Hz) and 3.95 (doublet, J=6.0 Hz), together 1H.

EXAMPLE 50

13-[2-Cyclopentyl-2-(5-methyl-2-pyrimidinylthio)acetoxy]milbemycin A$_4$ [Compound No. K-44: Step E (68%) - Step B (71%) - Step C (75%)]

Mass spectrum (m/z): 792 (M+), 756, 630, 540, 504.
Nuclear Magnetic Resonance Spectrum (CDCl$_3$, 200 MHz) δ ppm: 5.77–5.84 (2H, multiplet); 5.28–5.40 (4H, multiplet); 4.97 and 4.94 (together 1H, each doublet, J=10.5 Hz); 4.29 (1H, doublet, J=6.0 Hz); 3.96 (1H, doublet, J=6.0 Hz).

EXAMPLE 51

13-[2-(5-Chloro-2-pyrimidinylthio)-2-cyclopentylacetoxy]milbemycin A$_4$ [Compound No. K-45: Step E (68%) - Step B (67%) - Step C (64%)]

Mass spectrum (m/z): 772 (M+−40), 730, 681, 631, 520, 502.
Nuclear Magnetic Resonance Spectrum (CDCl$_3$, 200 MHz) δ ppm: 5.80–5.85 (2H, multiplet); 5.33–5.40 (4H, multiplet); 4.97 and 4.95 (together 1H, each doublet, J=10.5 Hz); 4.69 (1H, broad singlet); 3.96 (1H, doublet, J=6.2 Hz).

EXAMPLE 52

13-[2-Cyclopentyl-2-(4,6-dimethyl-2-pyrimidinylthio)acetoxy]milbemycin A$_4$ [Compound No. K-46: Step E (68%) - Step B (50%) - Step C (40%)]

Mass spectrum (m/z): 782 (M+−24), 752, 552, 516.
Nuclear Magnetic Resonance Spectrum (CDCl$_3$, 200 MHz) δ ppm: 5.77–5.82 (2H, multiplet); 5.30–5.40 (4H, multiplet); 4.95 (1H, doublet, J=10.3 Hz); 4.68 (1H, singlet); 3.96 (1H, doublet, J=6.2 Hz).

EXAMPLE 53

13-[2-Cyclopentyl-2-(4-methyl-2-pyrimidinylthio)acetoxy]milbemycin A$_4$ [Compound No. K-47: Step E (68%) - Step B (47%) - Step C (74%)]

Mass spectrum (m/z): 792 (M+), 756, 724, 504, 486.
Nuclear Magnetic Resonance Spectrum (CDCl$_3$, 200 MHz) δ ppm: 5.78–5.83 (2H, multiplet); 5.30–5.40 (4H, multiplet); 4.96 and 4.95 (together 1H, each doublet, J=10.5 Hz); 4.69 (1H, broad singlet); 3.96 (1H, doublet, J=6.2 Hz).

EXAMPLE 54

13-[2-Cyclohexyl-2 (2 pyrimidinylthio)acetoxy]milbemycin A$_4$ [Compound No. K-48: Step E (86%) - Step B (37%) - Step C (36%)]

Mass spectrum (m/z): 820 (M+), 504, 413, 315.

Nuclear Magnetic Resonance Spectrum (CDCl$_3$, 200 MHz) δ ppm: 6.66 (1H, singlet); 5.78–5.83 (2H, multiplet); 5.29–5.39 (4H, multiplet); 4.97 and 4.94 (together 1H, each doublet, J=10.4 Hz); 4.30 (1H, doublet, J=6.0 Hz); 3.96 (1H, doublet, J=6.0 Hz).

EXAMPLE 55

13-[2-Cyclohexyl-2-(4-methyl-2-pyrimidinylthio)acetoxy]milbemycin A$_4$ [Compound No. K-49: Step E (86%) - Step B (29%) - Step C (21%)]

Mass spectrum (m/z): 806 (M+), 540, 412.
Nuclear Magnetic Resonance Spectrum (CDCl$_3$, 200 MHz) δ ppm: 8.29 (1H, doublet, J=5.3 Hz); 6.80 (1H, doublet, J=5.1 Hz); 5.79–5.84 (2H, multiplet); 5.28–5.39 (4H, multiplet); 4.96 (1H, doublet, J=10.5 Hz); 4.29 (1H, doublet, J=6.0 Hz); 3.96 (1H, doublet, J=6.0 Hz).

EXAMPLE 56

13-[2-(5-Chloro-2-pyrimidinylthio)-2-(2,6-difluorophenyl)acetoxy]milbemycin A$_4$ [Compound No. K-50: Step E (40%) - Step B (40%) - Step C (16%)]

Mass spectrum (m/z): 724 (M+ −132), 540, 504, 279.
Nuclear Magnetic Resonance Spectrum (CDCl$_3$, 200 MHz) δ ppm: 5.73–5.79 (2H, multiplet); 5.26–5.39 (4H, multiplet); 4.98 and 4.93 (together 1H, each doublet, J=110 Hz); 4.28 (1H, multiplet); 4.07 (1H, singlet); 3.95 (1H, doublet, J=6.2 Hz).

EXAMPLE 57

13-[2-(2,6-Difluorophenyl)-2-(5-methyl-2-pyrimidinylthio)acetoxy]milbemycin A$_4$ [Compound No. K-51: Step E (*) - Step B (25%) - Step C (25%)]

Mass spectrum (m/z): 605 (M+ −231), 540, 412, 301.
Nuclear Magnetic Resonance Spectrum (CDCl$_3$, 200 MHz) δ ppm: 5.73–5.78 (2H, multiplet); 5.27–5.38 (4H, multiplet); 4.93 and 4.98 (together 1H, each doublet, J=12.4 Hz); 4.25–4.31 (1H, multiplet); 4.07 (1H, singlet); 3.95 (1H, doublet, J=6.2 Hz).

EXAMPLE 58

13-[2-(2,6-Difluorophenyl)-2-(4-methyl-2-pyrimidinylthio)acetoxy]milbemycin A$_4$ [Compound No. K-52: Step E (37%) - Step B (74%) - Step C (24%)]

Mass spectrum (m/z): 724 (M+ −112), 522, 307, 279.
Nuclear Magnetic Resonance Spectrum (CDCl$_3$, 200 MHz) δ ppm: 5.74–5.78 (2H, multiplet); 5.29–5.38 (4H, multiplet); 4.94 and 4.99 (together 1H, each doublet, J=11.4 Hz); 4.56 (2H, singlet); 3.95 (1H, doublet, J=6.02 Hz).

EXAMPLE 59

13-[2-(2,6-Difluorophenyl)-2-(4,6-dimethyl-2-pyrimidinylthio)acetoxy]milbemycin A$_4$ [Compound No. K-53: Step E (43%) - Step B (44%) - Step C (19%)]

Mass spectrum (m/z): 540 (M+ −310), 522, 311, 293.
Nuclear Magnetic Resonance Spectrum (CDCl$_3$, 200 MHz) δ ppm: 5.75–5.79 (2H, multiplet); 5.29–5.45 (4H, multiplet); 4.94 and 5.00 (together 1H, each doublet, J=10.4 Hz); 4.66 (2H, singlet); 3.95 (1H, doublet, J=6.3 Hz).

EXAMPLE 60

13-[2-Cyclohexyl-2-(5-methyl-2-pyrimidinylthio)acetoxy]milbemycin A$_4$ [Compound No. K-54: Step E (86%) - Step B (37%) - Step C (47%)]

Mass spectrum (m/z): 806 (M+), 540, 504, 440.
Nuclear Magnetic Resonance Spectrum (CDCl$_3$, 270 MHz) δ ppm: 8.30 (2H, singlet); 5.77–5.88 (2H, multiplet); 5.32–5.40 (4H, multiplet); 4.96 and 4.95 (together 1H, each doublet, J=10.5 Hz); 4.30 (1H, doublet, J=6.0 Hz); 3.96 (1H, doublet, J=6.0 Hz).

EXAMPLE 61

13-[2-(5-Chloro-2-pyrimidinylthio)-2-cyclohexylacetoxy]milbemycin A$_4$ [Compound No. K-55: Step E (86%) - Step B (50%) - Step C (32%)]

Mass spectrum (m/z): 826 (M+), 540, 504, 412.
Nuclear Magnetic Resonance Spectrum (CDCl$_3$, 270 MHz) δ ppm: 8.41 (2H, singlet); 5.80–5.85 (2H, multiplet); 5.35–5.39 (4H, multiplet); 4.97 (1H, doublet, J=10.5 Hz); 4.30 (1H, doublet, J=6.4 Hz); 3.97 (1H, doublet, J=6.4 Hz).

EXAMPLE 62

13-[2-Cyclohexyl-2-(2-pyrazinylthio)acetoxy]milbemycin A$_4$ [Compound No. K-56: Step E (86%) - Step B (50%) - Step C (16%)]

Mass spectrum (m/z): 792 (M+), 756, 504.
Nuclear Magnetic Resonance Spectrum (CDCl$_3$, 270 MHz) δ ppm: 5.76–5.87 (2H, multiplet); 5.29–5.39 (4H, multiplet); 4.95 (1H, doublet, J=10.5 Hz); 4.29 (1H, doublet, J=6.4 Hz); 3.95 (1H, doublet, J=6.4 Hz).

EXAMPLE 63

13-[2-Phenyl-2-(2-pyrazinylthio)acetoxy]milbemycin A$_4$ [Compound No. K-57: Step E (68%) - Step B (89%) - Step C (96%)]

Mass spectrum (m/z): 786 (M+), 540, 504.
Nuclear Magnetic Resonance Spectrum (CDCl$_3$, 200 MHz) δ ppm: 5.77–5.81 (2H, multiplet); 5.30–5.38 (4H, multiplet); 4.94 and 4.29 (together 1H, each doublet, J=10.6 Hz); 4.67 (1H, singlet); 3.95 (1H, doublet, J=6.2 Hz).

EXAMPLE 64

13-[2-phenyl-2-(2-pyrazinylthio)acetoxy]milbemycin A$_4$ [Compound No. K-58: Step E (68%) - Step B (68%) - Step C (84%)]

Nuclear Magnetic Resonance Spectrum (CDCl$_3$, 200 MHz) δ ppm: 5.79–5.84 (2H, multiplet); 5.30–5.39 (4H, multiplet); 4.96 and 4.94 (together 1H, each doublet, J=10.6 Hz); 4.29 (1H, doublet, J=6.3 Hz); 3.96 (1H, doublet, J=6.3 Hz).

EXAMPLE 65

13-[3-Cyclopentyl-2-(2-pyrimidinylthio)propionyloxy]milbemycin A$_4$ [Compound No. K-59: Step E (*) - Step B (55%) - Step C (58%)]

Mass spectrum (m/z): 792 (M+), 758, 541, 504, 412.
Nuclear Magnetic Resonance Spectrum (CDCl$_3$, 200 MHz) δ ppm: 5.78–5.83 (2H, multiplet); 5.28–5.42 (4H, multiplet); 4.94 and 4.97 (together 1H, each doublet, J=10.6 Hz); 4.27 (1H, multiplet); 4.07 (1H, doublet, J=1.26 Hz); 3.96 (1H, doublet, J=6.2 Hz).

EXAMPLE 66

13-[3-Cyclohexyl-2-(2-pyrimidinylthio)propionyloxy]-milbemycin $A_4$ [Compound No. K-60: Step E (*) - Step(*) - Step C (47%)]

Mass spectrum (m/z): 806 (M+), 678, 540, 522, 460, 412.
Nuclear Magnetic Resonance Spectrum (CDCl$_3$, 200 MHz) δ ppm: 5.79–5.98 (2H, multiplet); 5.29–5.44 (4H, multiplet); 4.94 (doublet, J=10.6 Hz) & 4.98 (doublet, J=10.5 Hz), together 1H; 4.06 (1H, broad singlet); 3.96 (1H, doublet, J=6.2 Hz).

EXAMPLE 67

13-[3-Methyl-2-(2-pyrimidinylthio)hexanoylmilbemycin $A_4$ [Compound No. K-61: Step E (58%) - Step B (58%) - Step C (84%)]

Mass spectrum (m/z): 780 (M+), 540, 412, 279, 223.
Nuclear Magnetic Resonance Spectrum (CDCl$_3$, 200 MHz) δ ppm: 5.77–5.84 (2H, multiplet); 5.28–5.43 (4H, multiplet); 4.97 and 4.99 (together 1H, each doublet, J=10.3 Hz); 4.26–4.33 (1H, multiplet); 4.05–4.08 (1H, broad); 3.96 (1H, doublet, J=6.0 Hz).

EXAMPLE 68

13-[2-Phenyl-2-(3-pyridazinylthio)acetoxy]milbemycin $A_4$ [Compound No. K-62: Step E (72%) - Step B (66%) - Step C (51%)]

Mass spectrum (m/z): 786 (M+), 672, 540, 522.
Nuclear Magnetic Resonance Spectrum (CDCl$_3$, 270 MHz) δ ppm: 5.77–5.83 (2H, multiplet); 5.28–5.38 (4H, multiplet); 4.95 and 4.87 (together 1H, each doublet, J=10.5 Hz); 4.09 (1H, singlet); 3.95 and 3.94 (together 1H, each doublet, J=6.04 Hz).

EXAMPLE 69

13-[3-Methyl-2-(3-pyridazinylthio)butyryloxy]milbemycin $A_4$ [Compound No. K-63: Step E (*) - Step B (18%) - Step C (52%)]

Mass spectrum (m/z): 752 (M+), 706, 540, 412.
Nuclear Magnetic Resonance Spectrum (CDCl$_3$, 270 MHz) δ ppm: 5.76–5.82 (2H, multiplet); 5.30–5.39 (4H, multiplet); 4.89 and 4.87 (together 1H, each doublet, J=6.85 Hz); 4.09 (1H, singlet); 3.96 (1H, doublet, J=6.0 Hz).

EXAMPLE 70

13-[2-(1,3-Benzodioxolan-5-yl)-2-pyrimidinylthio)acetoxy]milbemycin $A_4$ [Compound No. K-64: Step F (*) - Step C (7%)]

Mass spectrum: (m/z): 830 (M+), 652, 592, 540.
Nuclear Magnetic Resonance Spectrum (CDCl$_3$, 200 MHz) δ ppm: 5.74–5.83 (2H, multiplet); 5.28–5.41 (4H, multiplet); 4.94 and 4.96 (together 1H, each doublet, J=10.5 Hz); 4.08 (1H, broad singlet); 3.96 (1H, doublet, J=6.2 Hz).

EXAMPLE 71

13-[2-(2-Naphthyl)-2-(2-pyrimidinylthio)acetoxy]milbemycin $A_4$ [Compound No. K-65: Step E (*) - Step (60%) - Step (83%)]

Mass spectrum (m/z): 836 (M+), 800, 540, 412, 279.
Nuclear Magnetic Resonance Spectrum (CDCl$_3$, 200 MHz) δ ppm: 4.98 and 5.00 (together 1H, each doublet, J=10.4 Hz); 4.25–4.23 (1H, multiplet); 4.04 and 4.05 (together 1H, each singlet); 3.94 and 3.96 (together 1H, doublet, J=6.2 Hz).

EXAMPLE 72

13-[2-(4,6-Dimethoxy-1,3,5-triazin-2-yl)-2-phenylacetoxy]milbemycin $A_4$ [Compound No. K-66: Step E (68%) - Step B (*) - Step C (27%)]

Mass spectrum (m/z): 847 (M+), 811, 753, 676, 638, 596, 540, 504.
Nuclear Magnetic Resonance Spectrum (CDCl$_3$, 200 MHz) δ ppm: 5.76–5.82 (2H, multiplet); 5.30–5.39 (4H, multiplet); 4.95 and 4.94 (together 1H, each doublet, J=10.5 Hz); 4.29 (1H, triplet, J=7.1 Hz).

EXAMPLE 73

13-[(2S)-2-Phenyl-2-(2-pyrimidinylthio)acetoxy]milbemycin $A_4$ [Compound No. K-67: Step E (50%) - Step B (70%) - Step B (61%)]

Mass spectrum (m/z): 786 (M+), 658, 540, 522, 504.
Nuclear Magnetic Resonance Spectrum (CDCl$_3$, 270 MHz) δ ppm: 4.92 (1H, doublet, J=10.5 Hz); 4.28 (1H, doublet, J=6.3 Hz); 4.05 (1H, broad singlet); 3.95 (1H, doublet, J=6.3 Hz).

EXAMPLE 74

13-[2-(1,4-Benzodioxan-6-yl)-2-pyrimidinylthio)acetoxy]milbemycin $A_4$ [Compound No. K-69: Step F (34%) - Step C (41%)]

Mass spectrum (m/z): 844 (M+), 810, 606, 540, 412.
Nuclear Magnetic Resonance Spectrum (CDCl$_3$, 200 MHz) δ ppm: 5.73–5.82 (2H, multiplet); 5.25–5.42 (4H, multiplet); 4.93 and 4.95 (together 1H, each doublet, J=10.5 Hz); 4.07 (1H, singlet); 3.96 (1H, doublet, J=6.2 Hz).

EXAMPLE 75

13-[2-(6-Methoxy-3-pyridazinylthio)-2-phenylacetoxy]milbemycin $A_4$ [Compound No. K-70: Step E (72%) - Step B (*) - Step C (22%)]

Mass spectrum (m/z): 816 (M+), 702, 654, 620.
Nuclear Magnetic Resonance Spectrum (CDCl$_3$, 270 MHz) δ ppm: 5.77–5.89 (2H, multiplet); 5.28–5.38 (4H, multiplet); 4.93 and 4.89 (together 1H, each doublet, J=10.5 Hz); 3.95 and 3.94 (together 1H, each doublet, J=6.4 Hz).

EXAMPLE 76

13-[2-(6-Methoxy-3-pyridazinylthio)-3-methylbutyryloxy]milbemycin $A_4$ [Compound No. K-71: Step E (58%) - Step B (*) - Step C (2%)]

Mass spectrum (m/z): 782 (M+), 540, 412.
Nuclear Magnetic Resonance Spectrum (CDCl$_3$, 270 MHz) δ ppm: 5.76–5.83 (2H, multiplet); 5.34–5.39 (4H, multiplet); 4.97 and 4.94 (together 1H, each doublet, J=10.1 Hz); 4.29 (1H, doublet, J=5.2 Hz); 3.96 (1H, doublet, J=6.4 Hz).

EXAMPLE 77

13-[2-(6-Chloro-3-pyridazinylthio)-2-phenylacetoxy]milbemycin $A_4$ [Compound No. K-72: Step E (86%) - Step B (54%) - Step C (57%)]

Mass spectrum (m/z): 540 (M+ −280), 522, 504.
Mass spectrum (m/z): 820 (M+ −63), 706, 672, 640.
Nuclear Magnetic Resonance Spectrum (CDCl$_3$, 270 MHz) δ ppm: 5.76–5.79 (2H, multiplet); 5.28–5.38 (4H, multiplet); 4.92 and 4.89 (together 1H, each doublet, J=10.5 Hz); 4.28 (1H, broad singlet); 4.07 (1H, singlet); 3.95 and 3.94 (together 1H, each doublet, J=6.5 Hz).

EXAMPLE 78

13-[2-(6-Chloro-3-pyridazinylthio)-3-methylbutyryloxy]milbemycin $A_4$ [Compound No. K-73: Step E (58%) - Step B (*) - Step C (24%)]

Mass spectrum (m/z): 786 (M+), 540, 522, 412.
Nuclear Magnetic Resonance Spectrum (CDCl$_3$, 270 MHz) δ ppm: 5.76–5.87 (2H, multiplet); 5.30–5.39 (4H, multiplet); 4.96 and 4.93 (together 1H, each doublet, J=10.5 Hz); 4.29 (1H, triplet, J=6.4 Hz); 4.07 (1H, singlet); 3.96 (1H, doublet, J=6.4 Hz).

EXAMPLE 79

13-[2-(6-Methyl-3-pyridazinylthio)-2-phenylacetoxy]milbemycin $A_4$ [Compound No. K-74: Step E (86%) - Step B (*) - Step C (28%)]

Mass spectrum (m/z): 768 (M+ −32), 666, 522.
Nuclear Magnetic Resonance Spectrum (CDCl$_3$, 270 MHz) δ ppm: 5.75–5.79 (2H, multiplet); 5.28–5.39 (4H, multiplet); 4.94 and 4.88 (together 1H, each doublet, J=10.5 Hz); 4.27 (1H, triplet, J=6.5 Hz); 4.05 (1H, broad singlet); 3.95 and 3.94 (together 1H, each doublet, J=6.5 Hz).

EXAMPLE 80

13-[3-Methyl-2-(6-methyl-3-pyridazinylthio)butyryloxy]milbemycin $A_4$ [Compound No. K-75: Step E (58%) - Step B (*) - Step C (2%)]

Mass spectrum (m/z): 766 (M+), 540, 412.
Nuclear Magnetic Resonance Spectrum (CDCl$_3$, 270 MHz) δ ppm: 5.78–5.82 (2H, multiplet); 5.30–5.39 (4H, multiplet); 4.98 (doublet, J 10.3 Hz) & 4.90 (doublet, J=9.3 Hz), together 1H; 4.06 (1H, singlet); 3.96 (1H, doublet, J=6.0 Hz).

EXAMPLE 81

13-[2-Methyl-2-(2-pyrimidinylthio)propionyloxy]milbemycin $A_4$ [Compound No. L-76: Step E (72%) - Step B (11%) - Step C (36%)]

Mass spectrum (m/z): 739 (M+), 704, 626, 540.
Nuclear Magnetic Resonance Spectrum (CDCl$_3$, 270 MHz) δ ppm: 4.94 (1H, doublet, J=10.5 Hz); 4.29 (1H, doublet, J=6.0 Hz); 4.02 (1H, broad singlet); 3.95 (1H, doublet, J=6.0 Hz).

EXAMPLE 82

13-[(2R)-3-Methyl-2-(2-pyrimidinylthio)butyryloxy]milbemycin $A_4$ [Compound No. K-77: Step E (66%) - Step B (39%) - Step C (62%)]

Mass spectrum (m/z): 752 (M+), 640, 558, 540, 522.
Nuclear Magnetic Resonance Spectrum (CDCl$_3$, 270 MHz) δ ppm: 4.99 (1H, doublet, J=10.5); 4.40 (1H, doublet, J=6.4 Hz); 4.29 (1H, triplet, J=6.0 Hz); 4.06 (1H, singlet); 3.96 (1H, doublet, J=6.0 Hz).

EXAMPLE 83

13-[(2S)-3-Methyl-2-pyrimidinylthio)butyryloxy]milbemycin $A_4$ [Compound No. K-78: Step E (52%) - Step B (50%) - Step C (91%)]

Mass spectrum (m/z): 752 (M+), 716, 540, 522, 504.
Nuclear Magnetic Resonance Spectrum (CDCl$_3$, 270 MHz) δ ppm: 4.96 (1H, doublet, J=10 5); 4.43 (1H, doublet, J=6.5 Hz); 4.29 (1H, doublet, J=5.8 Hz); 4.03 (1H, broad singlet); 3.96 (1H, doublet, J=5.8 Hz).

EXAMPLE 84

13-[1-(2-Pyrimidinylthio)cyclopentanecarbonyloxy]milbemycin $A_4$ [Compound No. N-79: Step F (69%) - Step C (51%)]

Mass spectrum (m/z): 656 (M+ −110), 638, 540, 522.
Nuclear Magnetic Resonance Spectrum (CDCl$_3$, 200 MHz) δ ppm: 4.95 and 4.98 (together 1H, each doublet, J=10.5 Hz); 4.29 (1H, doublet, J=6.0 Hz); 4.03 (1H, broad singlet); 3.96 (1H, doublet, J=6.0 Hz).

EXAMPLE 85

13-[2-Ethyl-2-(2-pyrimidinylthio)butyryloxy]milbemycin $A_4$ [Compound No. M-80: Step F (49%) - Step C (53%)]

Mass spectrum (m/z): 656 (M+ −110), 638, 540, 522.
Nuclear Magnetic Resonance Spectrum (CDCl$_3$, 200 MHz) δ ppm: 4.95 and 4.98 (together 1H, each doublet, J=10.5 Hz); 4.29 (1H, doublet, J=6.0 Hz); 4.03 (1H, broad singlet); 3.96 (1H, doublet, J=6.0 Hz).

EXAMPLE 86

13-[1-(2-Pyrimidinylthio)cyclobutanecarbonyloxy]milbemycin $A_4$ [Compound No. N-81: Step F (24%) - Step (45%)]

Mass spectrum (m/z): 751 (M+), 540, 522, 504.
Nuclear Magnetic Resonance Spectrum (CDCl$_3$, 200 MHz) δ ppm: 4.94 (1H, doublet, J=10.7 Hz); 4.28 (1H, doublet, J=6.0 Hz); 4.04 (1H, broad singlet); 3.95 (1H, doublet, J=6.0 Hz).

EXAMPLE 87

13-[2-(2-Chlorophenyl)-2-(3-pyridazinylthio)acetoxy]milbemycin $A_4$ [Compound No. K-82: Step E (72%) - Step B (*) - Step C (5.2%)]

Mass spectrum (m/z): 766 (M+ −44), 726, 522.
Nuclear Magnetic Resonance Spectrum (CDCl$_3$, 270 MHz) δ ppm: 5.76–5.79 (multiplet); 5.26–5.39 (4H, multiplet); 4.89 (1H, doublet, J=10.5 Hz); 4.27 (1H, broad singlet); 3.94 (1H, doublet, J=6.04 Hz).

EXAMPLE 88

13-[2-(2-Chlorophenyl)-2-(3-pyridazinylthio)acetoxy]milbemycin $A_4$ [Compound No. K-83: Step E (72%) - Step B (*) - Step C (4%)]

Mass spectrum (m/z): 770 (M+ −50), 724, 706, 540.
Nuclear Magnetic Resonance Spectrum (CDCl$_3$, 270 MHz) δ ppm: 5.72–5.80 (2H, multiplet); 5.30–5.38 (4H, multiplet); 4.98 (1H, doublet, J=10.5 Hz); 4.28 (1H, broad singlet); 4.01 (1H, singlet); 3.95 (1H, doublet, J=6.5 Hz).

EXAMPLE 89

13-[2-(2-Chlorophenyl) 2-(6-methyl-3-Pyridazinylthio)acetoxy]milbemycin $A_4$ [Compound No. K-84: Step E (72%) - Step B (*) - Step C (6%)]

Mass spectrum (m/z): 796 (M+ −38), 755, 540, 522.
Nuclear Magnetic Resonance Spectrum (CDCl$_3$, 270 MHz) δ ppm: 5.71–5.80 (2H, multiplet); 5.25–5.38 (4H, multiplet); 4.97 and 4.90 (together 1H, each doublet, J=10.5); 4.28 (1H, broad singlet); 4.07 (1H, braod singlet); 3.95 and 3.94 (together 1H, each doublet, J=6.4 Hz).

EXAMPLE 90

13-[1-(2-Pyrimidinylthio)cyclohexanecarbonyloxy]-milbemycin $A_4$ [Compound No. N-85: Step F (7%) - Step C (50%)]

Mass spectrum (m/z): 778 (M+), 666, 540, 522, 412.
Nuclear Magnetic Resonance Spectrum (CDCl$_3$, 270 MHz) δ ppm: 5.73-5.87 (2H, multiplet); 5.22-5.41 (??H, multiplet); 4.94 (1H, doublet, J=10.7); 3.95 (1H, doublet, J=6.3 Hz).

EXAMPLE 91

13-[2-(3,6-Dimethyl-2-pyridazinylthio-2-phenylacetoxy]milbemycin $A_4$ [Compound No. K-86: Step E (57%) - Step B (100%) - Step C (67%)]

Mass spectrum (m/z): 814 (M+), 779, 676, 540, 412.
Nuclear Magnetic Resonance Spectrum (CDCl$_3$, 200 MHz) δ ppm: 5.74-5.79 (2H, multiplet); 5.24-5.37 (4H, multiplet); 4.90 and 4.99 (together 1H, each doublet, J=10.4 Hz); 4.09 (1H, singlet); 3.92 and 3.93 (together 1H, each doublet, J=6.1 Hz).

EXAMPLE 92

13-[2-(5-Ethyl-2-pyrimidinylthio)-2-phenylacetoxy]-milbemycin $A_4$ [Compound No. K-87: Step E (68%) - Step B (51%) - Step C (57%)]

Mass spectrum (m/z): 774 (M+−40), 692, 646, 564, 540, 522, 504.
Nuclear Magnetic Resonance Spectrum (CDCl$_3$, 200 MHz) δ ppm: 5.76-5.80 (2H, multiplet); 5.20-5.44 (4H, multiplet); 4.98 and 4.97 (together 1H, each doublet, J=10.5 Hz); 4.68 (1H, doublet, J=6.2 Hz); 4.29 (1H, triplet, J=7.0 Hz); 3.97 (1H, doublet, J=6.2 Hz).

EXAMPLE 93

13-[2-(5-Bromo-2-pyrimidinylthio)-2-phenylacetoxy]-milbemycin $A_4$ [Compound No. K-88: Step E (35%) - Step B (69%) - Step C (45%)]

Mass spectrum (m/z): 864 (M+), 736, 615, 540, 522, 504.
Nuclear Magnetic Resonance Spectrum (CDCl$_3$, 200 MHz) δ ppm: 5.72-5.80 (2H, multiplet); 5.23-5.38 (4H, multiplet); 4.94 and 4.92 (together 1H, each doublet, J=10.6 Hz); 4.08 (1H, doublet, J=7.0 Hz); 3.95 (1H, doublet, J=5.9 Hz).

EXAMPLE 94

13-[2-4-Methoxyphenyl)-2-(2-pyrimidinylthio)acetoxy]-milbemycin $A_4$ [Compound No. K-89: Step F (*) - Step C (13.5%)]

Mass spectrum (m/z): 816 (M+), 706, 652, 576, 540, 522.
Nuclear Magnetic Resonance Spectrum (CDCl$_3$, 200 MHz) δ ppm: 5.71-5.90 (2H, multiplet); 5.21-5.48 (4H, multiplet); 4.94 and 4.93 (together 1H, each doublet, J=10.5 Hz); 4.29 (1H, broad singlet); 3.95 (1H, doublet, J=6.2 Hz).

EXAMPLE 95

13-[3-Phenyl-2-(2-pyrimidinylthio]butyryloxy]milbemycin $A_4$ [Compound No. K-90 Step F (*) - Step C (9.0%)]

Mass spectrum (m/z): 814 (M+), 776, 686, 563, 540, 412.
Nuclear Magnetic Resonance Spectrum (CDCl$_3$, 200 MHz) δ ppm: 5.68-5.84 (2H, multiplet); 516-5.45 (4H, multiplet); 4.28 (1H, multiplet); 4.04 (1H, broad singlet); 3.95 (1H, doublet, J=6.2 Hz).

EXAMPLE 96

13-[2-(2-Methoxyphenyl)-2-(2-pyrimidinylthio)acetoxy]milbemycin $A_4$ [Compound No. K-91: Step F (*) - Step C (11.0%)]

Mass spectrum (m/z): 816 (M+), 786, 540, 521, 412.
Nuclear Magnetic Resonance Spectrum (CDCl$_3$, 200 MHz) δ ppm: 5.69-5.84 (2H, multiplet); 5.19-5.43 (4H, multiplet); 4.94 and 4.98 (together 1H, each doublet, J=10.4 Hz); 4.28 (1H, broad singlet); 4.06 (1H, singlet); 3.95 (1H, doublet, J=6.2 Hz).

EXAMPLE 97

13-[2-(6-Methyl-1,2,4-triazin-5-ylthio)-2-phenylacetoxy]milbemycin $A_4$ [Compound No. K-92: Step F (70%) - Step C (60%)]

Mass spectrum (m/z): 801 (M+), 676, 540.
Nuclear Magnetic Resonance Spectrum (CDCl$_3$, 270 MHz) δ ppm: 4.95 and 4.96 (together 1H, each doublet, J=10.5 Hz); 4.29 (together 1H, doublet, J=6.0 Hz); 3.95 and 3.96 (together 1H, each doublet, J=6.0 Hz).

EXAMPLE 98

13-[2-(5-Methyl-1,2,4-triazin-6-ylthio)-2-phenylacetoxy]milbemycin $A_4$ [Compound No. K-93: Step (*) - Step C (50%)]

Mass spectrum (m/z): 801 (M+), 676, 617, 540, 522.
Nuclear Magnetic Resonance Spectrum (CDCl$_3$, 270 MHz) δ ppm: 4.96 and 4.87 (together 1H, each doublet, J=10.4 Hz); 4.29 (1H, doublet, J=6.0 Hz); 3.95 and 3.96 (together 1H, each doublet, J=6.0 Hz).

EXAMPLE 99

13-[2,2-Bis(2-pyrimidinylthio)acetoxy]milbemycin $A_4$ [Compound No. K-94: Step E (38%) - Step B (41%) - Step C (43%)]

Mass spectrum (m/z): 598 (M+−222), 540, 522.
Nuclear Magnetic Resonance Spectrum (CDCl$_3$, 200 MHz) δ ppm: 5.73-5.82 (2H, multiplet); 5.27-5.39 (4H, multiplet); 4.98 (1H, doublet, J=10.5 Hz); 4.26-4.33 (1H, multiplet); 4.05 (1H, singlet); 3.96 (1H, doublet, J=6.2 Hz).

AGROCHEMICAL FORMULATIONS

Where the compounds of the invention are intended for agricultural or horticultural use, a variety of forms and formulations is possible, and these are exemplified in the following Examples. In these, all percentages are by weight, and the compounds of the present invention are identified by the numbers assigned to them in the foregoing Table 1.

EXAMPLE 100

Wettable Powders

A mixture comprising 10% of Compound No. K-10, 2.5% of sodium dodecylbenzenesulfonate, 2.5% of sodium lignin sulfonate and 85% of diatomaceous earth was thoroughly mixed and pulverized to make a wettable powder.

EXAMPLE 101

Emulsifiable Concentrates

A mixture of 5% of Compound No. K-3, 10% of Sorpol SM100 (a trade name for an emulsifying agent, Toho Chemical Inc.) and 85% of xylene was thoroughly mixed to make an emulsifiable concentrate.

EXAMPLE 102

Granules

A mixture comprising 3% of Compound No. K-17, 1% of white carbon, 5% of sodium lignin sulfonate and 91% of clay was thoroughly mixed and pulverized. Water was added to the resulting mixture, and the mixture was kneaded, granulated and dried to make granules.

EXAMPLE 103

Emulsifiable Concentrates

A mixture comprising 5% of Compound No. K-6, 45% of cyclohexanone, 11% of polyoxyethylene nonylphenyl ether, 4% of calcium dodecylbenzenesulfonate and 35% of methylnaphthalene was homogenously dissolved to make an emulsifiable concentrate.

EXAMPLE 104

Emulsifiable Concentrates

A mixture comprising 5% of Compound No. K-8, 10% of Sorpol SM100 (a trade name for an emulsifying agent, Toho Chemical Inc.) and 85% of xylene was thoroughly mixed to make an emulsifiable concentrate.

EXAMPLE 105

Wettable Powders

A mixture comprising 10% of Compound No. K-22, 5% of sodium lignin sulfonate, 3% of potassium laurylsulfate, 5% of highly dispersed silicic acid and 77% of kaoline was thoroughly mixed and pulverized to make a wettable powder.

EXAMPLE 106

Emulsifiable Concentrates

A mixture comprising 5% of Compound No. K-13, 3% of octylphenol polyethylene glycol ether (4 to 5 moles of ethylene oxide), 3% of sodium dodecylbenzenesulfonate, 4% of caster oil polyglycol ether (36 moles of ethylene oxide), 35% of cyclohexanone and 50% of xylene was homogeneously dissolved to make an emulsifiable concentrate.

EXAMPLE 107

Dusts

A mixture comprising 5% of Compound No. K-31 and 91% of talc was thoroughly mixed and pulverized to make a dust.

EXAMPLE 108

Emulsifiable Concentrates

A mixture comprising 1% of Compound No. K-3, 20% of Paracol KPS (emulsifying agent, Nippon Nyukazai Co. Ltd.) and 79% of xylene was thoroughly mixed to make an emulsifiable concentrate.

BIOLOGICAL ACTIVITY

The activity of the compounds of the invention is further illustrated by the following biological assay. In the following Tables 2, 3 and 4, all of Compounds (C1), (C2) and (C3), which are used as controls, for purposes of comparison have been discolosed in Japanese Patent Kokai Application No. Hei 1-104078 and have the formulae shown below. Compounds (C4), (C5) and (C6) are all included in the scope of Japanese Patent Kokai Application Hei 1-104078, but are not specifically disclosed therein. These compounds were newly synthesized by us and have the formulae shown below.

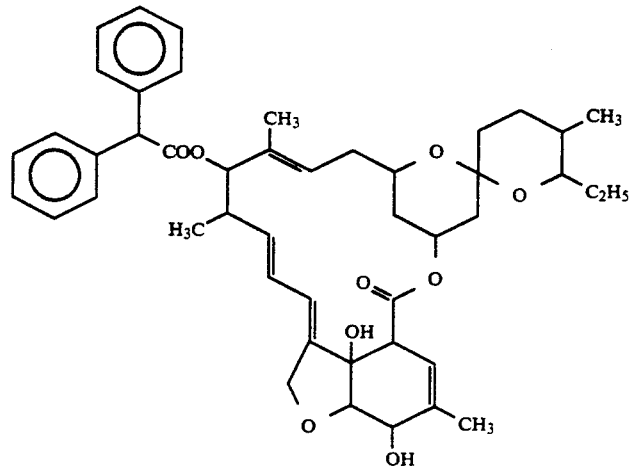

(C1)

-continued
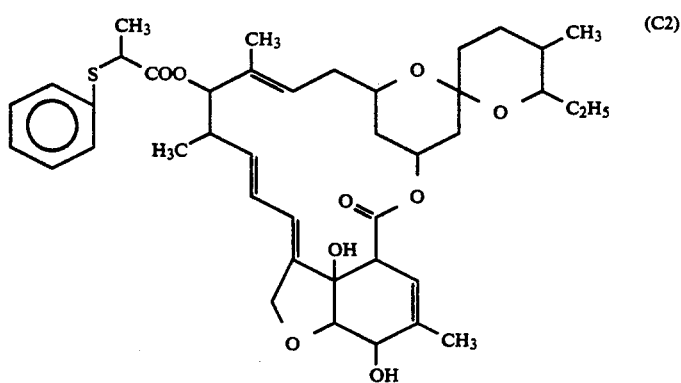
(C2)
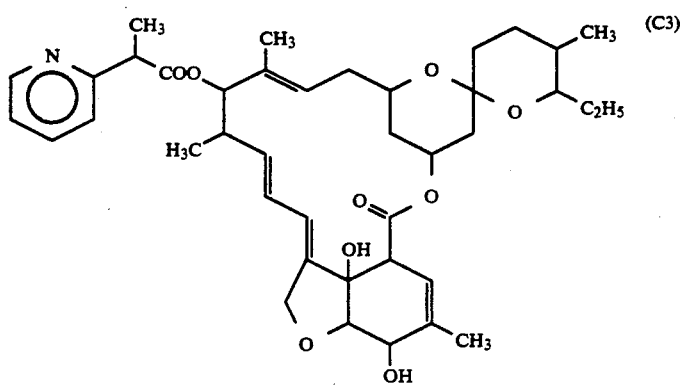
(C3)
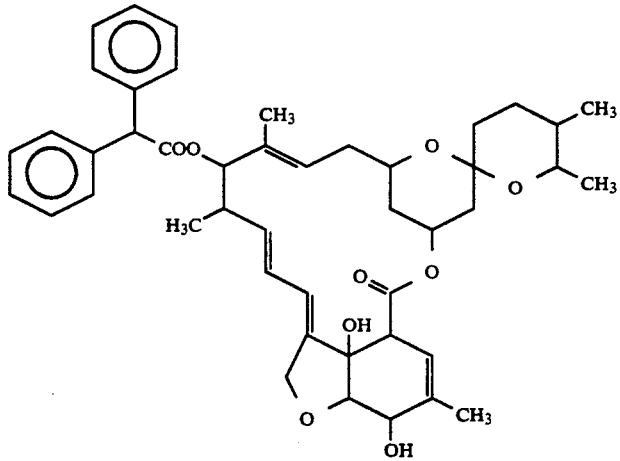
(C4)
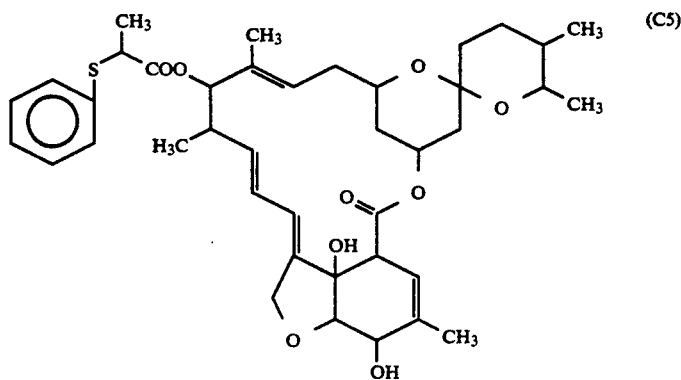
(C5)

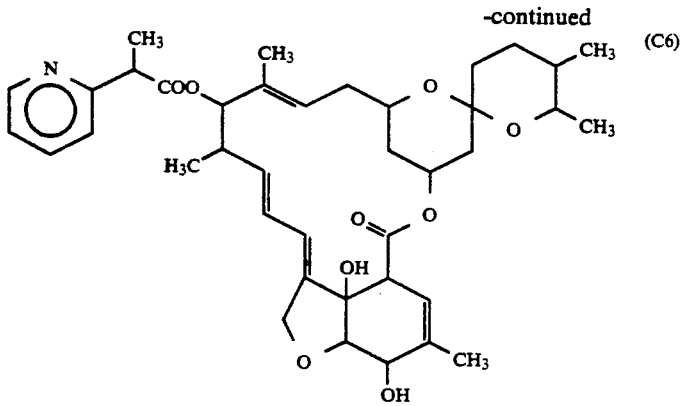

EXPERIMENT 1

Insecticidal Activity Against *Plutella mylostella*

Emulsifiable concentrates, prepared as described in Example 108, and containing 1% of the active ingredient, were diluted with water to bring the final concentration to 1 ppm. Cabbage leaves were immersed in the resulting mixtures for 10 seconds and then air-dried, after which each leaf was placed in a polyethylene cup having a diameter of 8 cm. Ten 3 day old larvae of *Plutella mylostella* were put into each cup, which was then capped. The cup was allowed to stand in a thermostat kept at 25° C. for 3 days, after which the percentage mortality (including symptoms of distress) was determined. Each test was carried out in duplicate in parallel. The results are shown in Table 2, in which the compounds of the invention are identified by the numbers assigned to them in the foregoing Table 1.

TABLE 2

| Cpd. No. | Mortality (%) |
|---|---|
| K-3 | 95 |
| K-4 | 100 |
| K-6 | 100 |
| K-7 | 100 |
| K-8 | 95 |
| K-9 | 100 |
| K-10 | 100 |
| K-11 | 100 |
| K-12 | 100 |
| K-13 | 100 |
| K-14 | 100 |
| K-15 | 100 |
| K-16 | 90 |
| K-17 | 100 |
| K-18 | 100 |
| K-19 | 100 |
| K-20 | 100 |
| K-21 | 100 |
| K-22 | 100 |
| K-23 | 100 |
| K-24 | 100 |
| K-25 | 100 |
| K-26 | 100 |
| K-28 | 90 |
| K-29 | 100 |
| K-30 | 100 |
| K-31 | 100 |
| K-32 | 100 |
| K-34 | 100 |
| K-35 | 95 |
| K-36 | 100 |
| K-38 | 100 |
| K-39 | 100 |
| K-40 | 100 |
| K-42 | 100 |
| K-43 | 95 |
| K-44 | 100 |
| K-45 | 100 |
| K-46 | 100 |
| K-47 | 100 |
| K-48 | 90 |
| K-49 | 100 |
| K-50 | 100 |
| K-51 | 100 |
| K-52 | 100 |
| K-53 | 100 |
| K-54 | 90 |
| K-56 | 100 |
| K-57 | 100 |
| K-59 | 100 |
| K-60 | 95 |
| K-61 | 95 |
| K-62 | 100 |
| K-64 | 100 |
| K-65 | 100 |
| K-66 | 100 |
| K-67 | 100 |
| K-68 | 100 |
| K-69 | 100 |
| K-70 | 100 |
| K-74 | 95 |
| K-77 | 100 |
| K-78 | 95 |
| N-79 | 95 |
| M-80 | 95 |
| N-81 | 95 |
| K-84 | 100 |
| K-86 | 100 |
| K-87 | 100 |
| K-88 | 95 |
| K-89 | 100 |
| K-90 | 95 |
| K-91 | 100 |
| K-92 | 100 |
| K-93 | 100 |
| K-94 | 95 |
| Control (C1) | 50 |
| Control (C2) | 20 |
| Control (C3) | 0 |
| Control (C4) | 50 |
| Control (C5) | 30 |
| Control (C6) | 10 |

EXPERIMENT 2

Insecticidal Activity Against *Spodoptera litura*

Emulsifiable concentrates, prepared as described in Example 108, and containing 1% of the active ingredient, were diluted with water to bring the final concentration to 10 ppm. 5 g of an artificial feed (Insecta L) were immersed in each of the resulting mixtures for 20 seconds, and the feed was then air-dried. It was then placed in a polyethylene cup having a diameter of 8 cm. Ten 3 day old larvae of *Spodoptera litura* were put into each cup, which was then capped. The cup was allowed to stand in a thermostat kept at 25° C. for 3 days, after which the percentage mortality (including symptoms of distress) was determined. Each test was carried out in duplicate in parallel. The results are shown in Table 3.

TABLE 3

| Cpd. No. | Mortality (%) |
|---|---|
| K-1 | 100 |
| K-2 | 100 |
| K-3 | 100 |
| K-4 | 100 |
| K-5 | 90 |
| K-6 | 100 |
| K-7 | 100 |
| K-8 | 100 |
| K-9 | 95 |
| K-11 | 100 |
| K-13 | 100 |
| K-14 | 100 |
| K-16 | 95 |
| K-21 | 100 |
| K-22 | 100 |
| K-25 | 100 |
| K-27 | 90 |
| K-28 | 100 |
| K-33 | 90 |
| K-40 | 100 |
| K-42 | 100 |
| K-43 | 100 |
| K-44 | 85 |
| K-47 | 95 |
| K-51 | 95 |
| K-59 | 95 |
| K-60 | 80 |
| K-61 | 100 |
| K-62 | 100 |
| K-63 | 100 |
| K-64 | 90 |
| K-66 | 100 |
| K-67 | 100 |
| K-68 | 100 |
| K-69 | 100 |
| K-70 | 100 |
| K-71 | 100 |
| K-72 | 100 |
| K-73 | 100 |
| K-74 | 100 |
| K-75 | 95 |
| L-76 | 100 |
| K-77 | 100 |
| K-78 | 100 |
| N-79 | 100 |
| M-80 | 100 |
| N-81 | 100 |
| K-82 | 100 |
| K-83 | 100 |
| K-84 | 100 |
| N-85 | 100 |
| N-88 | 80 |
| K-90 | 85 |
| K-93 | 100 |
| Control 1 | 55 |
| Control 2 | 10 |
| Control 3 | 10 |
| Control 4 | 60 |
| Control 5 | 20 |
| Control 6 | 5 |

EXPERIMENT 3

Insecticidal Activity Against *Adoxophyes orana*

Emulsifiable concentrates, prepared as described in Example 108, and containing 1% of the active ingredient, were diluted with water to bring the final concentration to 10 ppm. 5 g of an artificial feed (Insecta L) were immersed in each of the resulting mixtures for 20 seconds, and the feed was then air-dried. It was then placed in a polyethylene cup having a diameter of 8 cm. Ten 4 day old larvae of *Adoxophyes orana* were put into each cup, which was then capped. The cup was allowed to stand in a thermostat kept at 25° C. for 5 days, after which the percentage mortality (including symptoms of distress) was determined. Each test was carried out in duplicate in parallel. The results are shown in Table 4.

TABLE 4

| Cpd. No. | Mortality (%) |
|---|---|
| K-1 | 100 |
| K-2 | 100 |
| K-3 | 100 |
| K-4 | 100 |
| K-5 | 100 |
| K-6 | 100 |
| K-7 | 100 |
| K-8 | 100 |
| K-9 | 100 |
| K-10 | 100 |
| K-11 | 100 |
| K-12 | 100 |
| K-13 | 100 |
| K-14 | 95 |
| K-15 | 100 |
| K-16 | 100 |
| K-17 | 100 |
| K-18 | 95 |
| K-19 | 95 |
| K-20 | 100 |
| K-21 | 100 |
| K-22 | 100 |
| K-23 | 95 |
| K-24 | 100 |
| K-25 | 90 |
| K-26 | 100 |
| K-27 | 100 |
| K-28 | 100 |
| K-32 | 100 |
| K-33 | 100 |
| K-34 | 100 |
| K-37 | 100 |
| K-38 | 100 |
| K-39 | 100 |
| K-40 | 100 |
| K-42 | 100 |
| K-43 | 100 |
| K-44 | 100 |
| K-45 | 100 |
| K-46 | 100 |
| K-47 | 100 |
| K-48 | 95 |
| K-49 | 100 |
| K-50 | 100 |
| K-51 | 100 |
| K-52 | 100 |
| K-53 | 100 |
| K-54 | 100 |
| K-55 | 100 |
| K-56 | 100 |
| K-57 | 100 |
| K-58 | 100 |
| K-59 | 100 |
| K-61 | 100 |
| K-62 | 100 |
| K-63 | 100 |
| K-64 | 95 |
| K-66 | 100 |
| K-67 | 100 |
| K-68 | 95 |
| K-69 | 95 |
| K-71 | 100 |
| K-72 | 95 |
| K-73 | 95 |
| K-74 | 100 |
| K-75 | 100 |

TABLE 4-continued

| Cpd. No. | Mortality (%) |
|---|---|
| L-76 | 100 |
| K-77 | 100 |
| K-78 | 100 |
| N-79 | 100 |
| M-80 | 100 |
| N-81 | 100 |
| K-82 | 100 |
| K-83 | 100 |
| K-84 | 100 |
| N-85 | 100 |
| K-88 | 95 |
| Control 1 | 60 |
| Control 2 | 10 |
| Control 3 | 0 |
| Control 4 | 60 |
| Control 5 | 10 |
| Control 6 | 20 |

We claim:

1. Compounds having the formula (I):

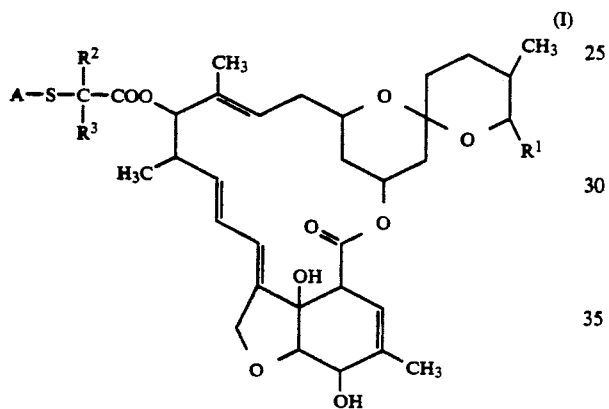

wherein:

$R^1$ represents a methyl, ethyl or isopropyl group;

$R^2$ represents:

an alkyl group having from 1 to 6 carbon atoms;

an aralkyl group, in which an alkyl group having from 1 to 3 carbon atoms is substituted by at least one carbocyclic aryl group having from 6 to 10 carbon atoms, said aryl group being unsubstituted or being substituted by at least one substituent selected from the group consisting of methyl and ethyl groups;

a cycloalkyl group having from 3 to 6 carbon atoms;

a cycloalkylmethyl group in which the cycloalkyl part has from 3 to 6 carbon atoms;

a carbocyclic aryl group which has from 6 to 10 ring carbon atoms and which is unsubstituted or is substituted by at least one substituent selected from the group consisting of methyl groups, ethyl groups, a haloalkyl group having 1 or 2 carbon atoms, methoxy groups, ethoxy groups, halogen atoms and amino groups;

a heterocyclic group in which a 5- or 6-membered alicyclic ring containing 1 or 2 oxygen atoms is condensed with benzene ring; or a group of formula $R^4$—S—, in which $R^4$ represents a 6-membered aromatic heterocyclic group containing 2 nitrogen atoms;

$R^3$ represents a hydrogen atom, a methyl group or an ethyl group; or $R^2$ together with $R^3$ represents a group of formula —$(CH_2)_n$—, wherein n represents the integer 3, 4 or 5; and A represents a 6-membered aromatic heterocyclic group containing 2 or 3 nitrogen atoms which is unsubstituted or is substituted by at least one substituent selected from the group consisting of alkyl groups having from 1 to 4 carbon atoms, methoxy groups, ethoxy groups and halogen atoms;

and salts thereof.

2. The compound of claim 1, wherein $R^2$ represents:

an alkyl group having from 2 to 5 carbon atoms;

an arylmethyl group in which the aryl part has from 6 to 10 carbon atoms;

a cycloalkyl group having 5 or 6 carbon atoms;

a cycloalkylmethyl group in which the cycloalkyl part has 5 or 6 carbon atoms;

a phenyl group or a 2-naphthyl group which is unsubstituted or is substituted by 1 or 2 substituents selected from the group consisting of methyl groups, trifluoromethyl groups, methoxy groups, fluorine atoms, chlorine atoms and amino groups;

a benzene ring condensed with a 5- or 6-membered alicyclic group containing 1 or 2 oxygen atoms; or a 6-membered aromatic heterocyclic group containing 2 nitrogen atoms.

3. The compound of claim 1, wherein $R^3$ represents a hydrogen atom, a methyl group or an ethyl group.

4. The compound of claim 1, wherein $R^2$ and $R^3$ together represent a trimethylene group.

5. The compound of claim 1, wherein A represents a 6-membered aromatic heterocyclic group containing 2 or 3 nitrogen atoms which is unsubstituted or is substituted by at least one substituent selected from the group consisting of methyl groups, ethyl groups, methoxy groups, ethoxy groups and halogen atoms.

6. The compound of claim 1, wherein:

$R^2$ represents:

an alkyl group having from 2 to 5 carbon atoms;

an arylmethyl group in which the aryl part has from 6 to 10 carbon atoms;

a cycloalkyl group having 5 or 6 carbon atoms;

a cycloalkylmethyl group in which the cycloalkyl part has 5 or 6 carbon atoms;

a phenyl group or a 2-naphthyl group which is unsubstituted or is substituted by 1 or 2 substituents selected from the group consisting of methyl groups, trifluoromethyl groups, methoxy groups, fluorine atoms, chlorine atoms and amino groups;

a benzene ring condensed with a 5- or 6-membered alicyclic group containing 1 or 2 oxygen atoms; or a 6-membered aromatic heterocyclic group containing 2 nitrogen atoms;

$R^3$ represents a hydrogen atom, a methyl group or an ethyl group;

$R^2$ and $R^3$ together represent a trimethylene group; and

A represents a 6-membered aromatic heterocyclic group containing 2 or 3 nitrogen atoms which is unsubstituted or is substituted by at least one substituent selected from the group consisting of methyl groups, ethyl groups, methoxy groups, ethoxy groups and halogen atoms.

7. The compound of claim 1, wherein $R^1$ represents a methyl or ethyl group.

8. The compound of claim 1, wherein $R^2$ represents: an alkyl group having from 3 to 5 carbon atoms; a 1-methylbenzyl group; a phenyl group which is unsubstituted or is substituted by 1 or 2 substituents selected from the group consisting of methyl groups, trifluoromethyl groups, methoxy groups, fluorine atoms, chlorine atoms and amino groups; a 2-naphthyl group; a 1,3-benzodioxolan-5-yl group; or a 1,4-benzodioxan-6-yl group.

9. The compound of claim 1, wherein $R^3$ represents a hydrogen atom.

10. The compound of claim 1, wherein A represents a 3-pyridazinyl group, a 2-pyridazinyl group, a 4-pyrimidinyl group, a 2-pyrazinyl group or a 1,3,5-triazin-2-yl group, each of which is unsubstituted or is substituted by 1 or 2 substituents selected from the group consisting of methyl groups, ethyl groups, methoxy groups, ethoxy groups and halogen atoms.

11. The compound of claim 1, wherein:
$R^1$ represents a methyl or ethyl group;
$R^2$ represents: an alkyl group having from 3 to 5 carbon atoms; a 1-methylbenzyl group; a phenyl group which is unsubstituted or is substituted by 1 or 2 substituents selected from the group consisting of methyl groups, trifluoromethyl groups, methoxy groups, fluorine atoms, chlorine atoms and amino groups; a 2-naphthyl group; a 1,3-benzodioxolan-5-yl group; or a 1,4-benzodioxan-6-yl group;
$R^3$ represents a hydrogen atom; and
A represents a 3-pyridazinyl group, a 2-pyridazinyl group, a 4-pyrimidinyl group, a 2-pyrazinyl group or a 1,3,5-triazin-2-yl group, each of which is unsubstituted or is substituted by 1 or 2 substituents selected from the group consisting of methyl groups, ethyl groups, methoxy groups, ethoxy groups and halogen atoms.

12. The compound of claim 1, wherein $R^2$ represents an isopropyl group or a phenyl group which is unsubstituted or is substituted by 1 or 2 substituents selected from the group consisting of methyl groups, trifluoromethyl groups, fluorine atoms and chlorine atoms at the 2-position and/or 6-position of the phenyl group.

13. The compound of claim 1, wherein A represents a 2-pyrimidinyl group.

14. The compound of claim 1, wherein:
$R^1$ represents a methyl or ethyl group;
$R^2$ represents an isopropyl group or a phenyl group which is unsubstituted or is substituted by 1 or 2 substituents selected from the group consisting of methyl groups, trifluoromethyl groups, fluorine atoms and chlorine atoms at the 2-position and/or 6-position of the phenyl group;
$R^3$ represents a hydrogen atom; and
A represents a 2-pyrimidinyl group.

15. The compound of claim 1, wherein $R^2$ represents an isopropyl or phenyl group.

16. The compound of claim 1, wherein:
$R^1$ represents a methyl or ethyl group;
$R^2$ represents an isopropyl or phenyl group;
$R^3$ represents a hydrogen atom; and
A represents a 2-pyrimidinyl group.

17. The compound of claim 1, selected from the group consisting of 13-[3-methyl-2-(2-pyrimidinylthio)butyryloxy]milbemycin $A_4$ and salts thereof.

18. The compound of claim 1, selected from the group consisting of 13-[2-phenyl-2-(2-pyrimidinylthio)acetoxy]milbemycin $A_4$ and salts thereof.

19. The compound of claim 1, selected from the group consisting of 13-[3-methyl-2-(2-pyrimidinylthio)butyryloxy]milbemycin $A_3$ and salts thereof.

20. The compound of claim 1, selected from the group consisting of 13-[2-phenyl-2-(2-pyrimidinylthio)acetoxy]milbemycin $A_3$ and salts thereof.

21. The compound of claim 1, selected from the group consisting of 13-[(2S)-2-phenyl-2-(2-pyrimidinylthio)acetoxy]milbemycin $A_4$ and salts thereof 22. The compound of claim 1, selected from the group consisting of 13-[(2R)-2-phenyl-2-(2-pyrimidinylthio)acetoxy]milbemycin $A_4$ and salts thereof.

23. The compound of claim 1, selected from the group consisting of 13-[(2R)-3-methyl-2-(2-pyrimidinylthio)butyryloxy]milbemycin $A_4$ and salts thereof.

24. The compound of claim 1, selected from the group consisting of 13-[(2S)-3-methyl-2-(2-pyrimidinylthio)butyryloxy]milbemycin $A_4$ and salts thereof.

25. An anthelmintic, acaricidal and insecticidal composition comprising an anthelmintic, acaricidal and insecticidal compound in admixture with an agriculturally or horticulturally acceptable carrier or diluent, wherein said compound is selected from the group consisting of compounds of formula (I) and salts thereof, as claimed in claim 1.

26. The composition of claim 25, wherein:
$R^2$ represents:
an alkyl group having from 2 to 5 carbon atoms;
an arylmethyl group in which the aryl part has from 6 to 10 carbon atoms;
a cycloalkyl group having 5 or 6 carbon atoms;
a cycloalkylmethyl group in which the cycloalkyl part has 5 or 6 carbon atoms;
a phenyl group or a 2-naphthyl group which is unsubstituted or is substituted by 1 or 2 substituents selected from the group consisting of methyl groups, trifluoromethyl groups, methoxy groups, fluorine atoms, chlorine atoms and amino groups;
a benzene ring condensed with a 5- or 6-membered alicyclic group containing 1 or 2 oxygen atoms; or
a 6-membered aromatic heterocyclic group containing 2 nitrogen atoms;
$R^3$ represents a hydrogen atom, a methyl group or an ethyl group;
$R^2$ and $R^3$ together represent a trimethylene group; and
A represents a 6-membered aromatic heterocyclic group containing 2 or 3 nitrogen atoms which is unsubstituted or is substituted by at least one substituent selected from the group consisting of methyl groups, ethyl groups, methoxy groups, ethoxy groups and halogen atoms.

27. The composition of claim 25, wherein:
$R^1$ represents a methyl or ethyl group;
$R^2$ represents: an alkyl group having from 3 to 5 carbon atoms; a 1-methylbenzyl group; a phenyl group which is unsubstituted or is substituted by 1 or 2 substituents selected from the group consisting of methyl groups, trifluoromethyl groups, methoxy groups, fluorine atoms, chlorine atoms and amino groups; a 2-naphthyl group; a 1,3-benzodioxolan-5-yl group; or a 1,4-benzodioxan-6-yl group;
$R^3$ represents a hydrogen atom; and A represents a 3-pyridazinyl group, a 2-pyridazinyl group, a 4-pyrimidinyl group, a 2-pyrazinyl group or a 1,3,5-triazin-2-yl group, each of which is unsubstituted or is substituted by 1 or 2 substituents selected from the group consisting of methyl groups, ethyl groups, methoxy groups, ethoxy groups and halogen atoms.

28. The composition of claim 25, wherein:
$R^1$ represents a methyl or ethyl group;
$R^2$ represents an isopropyl group or a phenyl group which is unsubstituted or is substituted by 1 or 2 substituents selected from the group consisting of methyl groups, trifluoromethyl groups, fluorine atoms and chlorine atoms at the 2-position and/or 6-position of the phenyl group;
$R^3$ represents a hydrogen atom; and
A represents a 2-pyrimidinyl group.

29. The composition of claim 25, wherein:
$R^1$ represents a methyl or ethyl group;
$R^2$ represents an isopropyl or phenyl group;
$R^3$ represents a hydrogen atom; and
A represents a 2-pyrimidinyl group.

30. The composition of claim 25, wherein the active compound is selected from the group consisting of:

13-[3-methyl-2-(2-pyrimidinylthio)butyryloxy]milbemycin $A_4$;
13-[2-phenyl-2-(2-pyrimidinylthio)acetoxy]milbemycin $A_4$;
13-[3-methyl-2-(2-pyrimidinylthio)butyryloxy]milbemycin $A_3$;
13-[2-phenyl-2-(2-pyrimidinylthio)acetoxy]milbemycin $A_3$;
13-[(2S)-2-phenyl-2-(2-pyrimidinylthio)acetoxy]milbemycin $A_4$;
13-[(2R)-2-phenyl-2-(2-pyrimidinylthio)acetoxy]milbemycin $A_4$;
13-[(2R)-3-methyl-2-(2-pyrimidinylthio)butyryloxy]milbemycin $A_4$;
13-[(2S)-3-methyl 2-(2-pyrimidinylthio)butyryloxy]milbemycin $A_4$;

and salts thereof.

31. A method of protecting plants from damage by parasites selected from the group consisting of acarids, helminths and insects, which comprises applying an active compound to said plants or to parts of or reproductive matter of said plants or to a locus including said plants or parts of said plants or reproductive matter of said plants, wherein the active compound is selected from the group consisting of compounds of formula (I) and salts thereof, as claimed in claim 1.

32. The method of claim 31, wherein:
$R^2$ represents:
an alkyl group having from 2 to 5 carbon atoms;
an arylmethyl group in which the aryl part has from 6 to 10 carbon atoms;
a cycloalkyl group having 5 or 6 carbon atoms;
a cycloalkylmethyl group in which the cycloalkyl part has 5 or 6 carbon atoms;
a phenyl group or a 2-naphthyl group which is unsubstituted or is substituted by 1 or 2 substituents selected from the group consisting of methyl groups, trifluoromethyl groups, methoxy groups, fluorine atoms, chlorine atoms and amino groups;

a benzene ring condensed with a 5- or 6-membered alicyclic group containing 1 or 2 oxygen atoms; or
a 6-membered aromatic heterocyclic group containing 2 nitrogen atoms;
$R^3$ represents a hydrogen atom, a methyl group or an ethyl group;
$R^2$ and $R^3$ together represent a trimethylene group; and
A represents a 6-membered aromatic heterocyclic group containing 2 or 3 nitrogen atoms which is unsubstituted or is substituted by at least one substituent selected from the group consisting of methyl groups, ethyl groups, methoxy groups, ethoxy groups and halogen atoms.

33. The method of claim 31, wherein:
$R^1$ represents a methyl or ethyl group;
$R^2$ represents: an alkyl group having from 3 to 5 carbon atoms; a 1-methylbenzyl group; a phenyl group which is unsubstituted or is substituted by 1 or 2 substituents selected from the group consisting of methyl groups, trifluoromethyl groups, methoxy groups, fluorine atoms, chlorine atoms and amino groups; a 2-naphthyl group; a 1,3-benzodioxolan-5-yl group; or a 1,4-benzodioxan-6-yl group;
$R^3$ represents a hydrogen atom; and
A represents a 3-pyridazinyl group, a 2-pyridazinyl group, a 4-pyrimidinyl group, a 2-pyrazinyl group or a 1,3,5-triazin-2-yl group, each of which is unsubstituted or is substituted by 1 or 2 substituents selected from the group consisting of methyl groups, ethyl groups, methoxy groups, ethoxy groups and halogen atoms.

34. The method of claim 31, wherein:
$R^1$ represents a methyl or ethyl group;
$R^2$ represents an isopropyl group or a phenyl group which is unsubstituted or is substituted by 1 or 2 substituents selected from the group consisting of methyl groups, trifluoromethyl groups, fluorine atoms and chlorine atoms at the 2-position and/or 6-position of the phenyl group;
$R^3$ represents a hydrogen atom; and
A represents a 2-pyrimidinyl group.

35. The method of claim 31, wherein:
$R^1$ represents a methyl or ethyl group;
$R^2$ represents an isopropyl or phenyl group;
$R^3$ represents a hydrogen atom; and
A represents a 2-pyrimidinyl group.

36. The method of claim 31, wherein the active compound is selected from the group consisting of:

13-[3-methyl-2-(2-pyrimidinylthio)butyryloxy]milbemycin $A_4$;
13-[2-phenyl-2-(2-pyrimidinylthio)acetoxy]milbemycin $A_4$;
13-[3-methyl-2-(2-pyrimidinylthio)butyryloxy]milbemycin $A_3$;
13-[2-phenyl-2-(2-pyrimidinylthio)acetoxy]milbemycin $A_3$;
13-[(2S) 2-phenyl-2-(2-pyrimidinylthio)acetoxy]milbemycin $A_4$;
13-[(2R) 2-phenyl-2-(2-pyrimidinylthio)acetoxy]milbemycin $A_4$;
13-[(2R)-3-methyl-2-(2-pyrimidinylthio)butyryloxy]milbemycin $A_4$;
13-[(2S)-3-methyl-2-(2-pyrimidinylthio)butyryloxy]milbemycin $A_4$;

and salts thereof.

* * * * *

UNITED STATES PATENT AND TRADEMARK OFFICE
CERTIFICATE OF CORRECTION

PATENT NO. : 5,276,033

DATED : January 4, 1994

INVENTOR(S) : Yanai et al

It is certified that error appears in the above-identified patent and that said Letters Patent is hereby corrected as shown below:

Title page, left column, in the line under "[22] Filed: Dec. 17, 1992" insert --[30]   Foreign Application Priority Data
         Dec. 18, 1991   [JP]   Japan.....3-334650--.

Signed and Sealed this

Fourteenth Day of February, 1995

Attest:

BRUCE LEHMAN

*Attesting Officer*             *Commissioner of Patents and Trademarks*